United States Patent [19]

Allais et al.

[11] 3,995,056
[45] Nov. 30, 1976

[54] BUTYRIC ACID DERIVATIVES FOR TREATING PAIN AND INFLAMMATION

[75] Inventors: Andre Allais, Les Lilas; Jean Meier, Coeuilly-Champigny; Jacques Dube, Eaubonne, all of France

[73] Assignee: Roussel-UCLAF, Paris, France

[22] Filed: Oct. 23, 1975

[21] Appl. No.: 624,733

Related U.S. Application Data

[62] Division of Ser. No. 284,575, Aug. 29, 1972, Pat. No. 3,931,302.

[30] Foreign Application Priority Data

Sept. 3, 1971    France .............................. 71.31902

[52] U.S. Cl. ................................. 424/317; 424/278; 424/308
[51] Int. Cl.² ................ A61K 31/19; A61K 31/235; A61K 31/335
[58] Field of Search ..................... 424/317, 308, 278

Primary Examiner—Stanley J. Friedman
Attorney, Agent, or Firm—Hammond & Littell

[57] ABSTRACT

Novel butyric acid derivatives of the formula

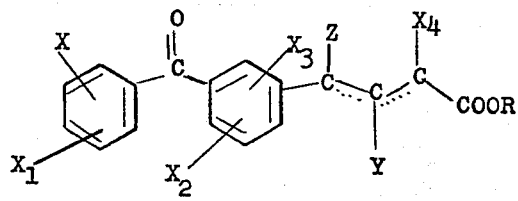

I wherein $X$, $X_1$, $X_2$ and $X_3$ are individually selected from the group consisting of hydrogen, halogen, lower alkyl of 1 to 5 carbon atoms, lower alkoxy of 1 to 5 carbon atoms, lower alkylthio of 1 to 5 carbon atoms, trifluoromethoxy, trifluoromethylthio, trifluoromethyl, OH and dilower alkylamino of 1 to 5 carbon atoms for each alkyl, R is selected from the group consisting of hydrogen, lower alkyl of 1 to 5 carbon atoms, o-carboxyphenyl, 2,3-dihydroxypropyl and

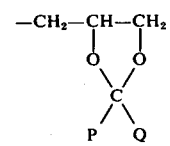

wherein P and Q are individually lower alkyl of 1 to 5 carbon atoms, Z and $X_4$ are individually selected from the group consisting of hydrogen and lower alkyl of 1 to 5 carbon atoms and Y is selected from the group consisting of hydrogen and —CH and the dotted line indicates the optional presence of a double bond when Y is hydrogen and when R is hydrogen or o-carboxyphenyl, the salts thereof with a non-toxic pharmaceutically acceptable mineral or orgaic base, which compounds have anti-inflammatory and analgesic activity and are substantially devoid of ulcerigenic activity and their preparation and novel intermediates formed therein.

7 Claims, No Drawings

BUTYRIC ACID DERIVATIVES FOR TREATING PAIN AND INFLAMMATION

PRIOR APPLICATION

This application is a division of copending, commonly assigned application Ser. No. 284,575 filed Aug. 29, 1972, now U.S. Pat. No. 3,931,302.

OBJECTS OF THE INVENTION

It is an object of the invention to provide the novel butyric acid derivatives of formula I and their salts with a non-toxic, pharmaceutically acceptable base where appropriate.

It is a further object of the invention to provide a novel process for the preparation of the butyric acid derivatives of formula I and to provide novel intermediates produced therein.

It is another object of the invention to provide novel analgesic and anti-inflammatory compositions.

It is an additional object of the invention to provide a novel method of relieving pain and inflammation in warmblooded animals.

These and other objects and advantages of the invention will become obvious from the following detailed description.

THE INVENTION

The novel butyric acid derivatives of the invention are selected from compounds of the formula

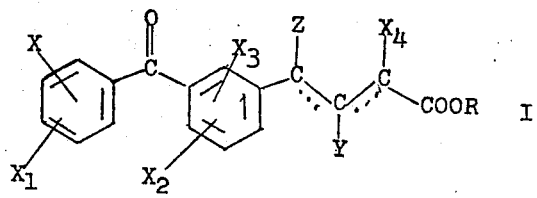

I wherein X, $X_1$, $X_2$ and $X_3$ are individually selected from the group consisting of hydrogen, halogen, lower alkyl of 1 to 5 carbon atoms, lower alkoxy of 1 to 5 carbon atoms, lower alkylthio of 1 to 5 carbon atoms, trifluoromethoxy, trifluoromethylthio, trifluoromethyl, OH and dilower alkylamino of 1 to 5 carbon atoms for each alkyl, R is selected from the group consisting of hydrogen, lower alkyl of 1 to 5 carbon atoms, O-carboxyphenyl, 2,3-dihydroxypropyl and

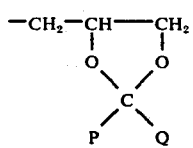

wherein P and Q are individually lower alkyl of 1 to 5 carbon atoms, Z and $X_4$ are individually selected from the group consisting of hydrogen and lower alkyl of 1 to 5 carbon atoms and Y is selected from the group consisting of hydrogen and —OH and the dotted line indicates the optional presence of a double bond when Y is hydrogen and when R is hydrogen or o-carboxyphenyl, and salts thereof with a non-toxic, pharmaceutically acceptable mineral or organic base.

In the compounds of the formula, X, $X_1$, and $X_2$ and $X_3$ can be in any possible position on the benzene rings and when they are halogen, they are preferably fluorine or chlorine and when they are alkyl, alkoxy or alkylthio, they are preferably methyl, ethyl, n-propyl, methoxy, ethoxy, methylthio or ethylthio. When there is a double bond present in the butyric acid chain, the compounds of formula I may be cis isomers or trans isomers.

Examples of non-toxic, pharmaceutically acceptable salts when R is hydrogen or o-carboxyphenyl are alkali metal salts such as sodium, potassium or lithium, alkaline earth metal salts such as calcium, ammonium or amine salts such as triethylamine.

Among the preferred compounds of formula I are those having a formula selected from the group consisting of

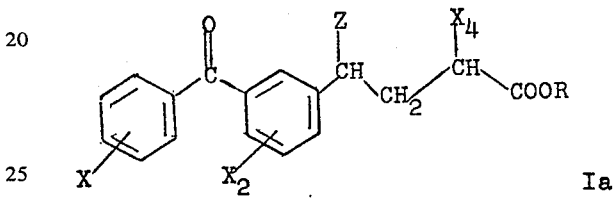

Ia wherein X and $X_2$ are individually selected from the group consisting of hydrogen, halogen, alkyl of 1 to 5 carbon atoms, alkoxy of 1 to 5 carbon atoms, alkylthio of 1 to 5 carbon atoms, trifluoromethyl, trifluoromethoxy and trifluoromethylthio, R is selected from the group consisting of hydrogen, alkyl of 1 to 5 carbon atoms, 2, 3-dihydroxypropyl and

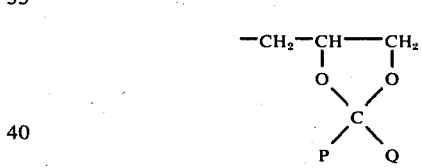

wherein P and Q are individually alkyl of 1 to 5 carbon atoms and $X_4$ and Z have the above definitions and the non-toxic, pharmaceutically acceptable salts thereof where R is hydrogen,

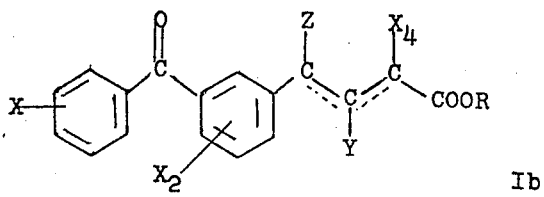

Ib wherein X, $X_2$, $X_4$, Y, Z and R have the above definitions with the dotted line representing, when Y is hydrogen, a double bond in either αβ or βγ to the carboxylic group and the non-toxic, pharmaceutically acceptable salts thereof when R is hydrogen, and

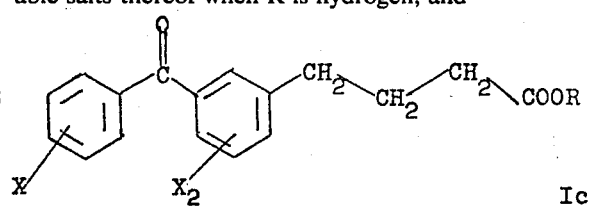

Ic wherein X, X₂ and R have the above definitions and the non-toxic, pharmaceutically acceptable salts thereof when R is hydrogen.

The most preferred compounds of formula I are 4-(3'-p-chlorobenzoyl-2'-methyl-phenyl)-butyric acid and 4-(3'-p-chlorobenzoyl-2'-methyl-phenyl)-2-butenoic acid.

The novel process of the invention depends upon the nature of the particular substituents. The process for the preparation of compounds of formula Ia comprises reacting a m-benzoylphenyl-propionic acid of the formula

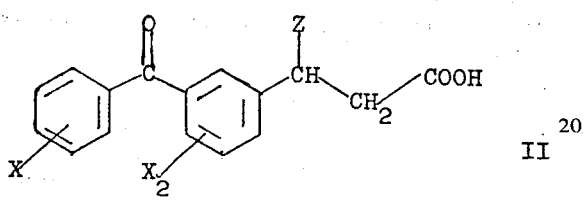

II wherein X, X₂ and Z have the definition as in formula Ia with a chlorinating agent to form the corresponding acid chloride of the formula

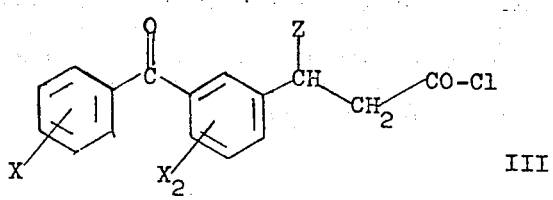

III reacting the latter with a diazoalkane of the formula X₄—CHN₂ wherein X₄ has the above definition to obtain a diazoketone of the formula

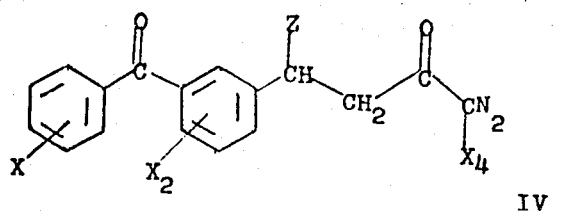

IV reacting the latter with a compound of the formula R₁OH wherein R₁ is selected from the group consisting of hydrogen, alkyl of 1 to 5 carbon atoms and

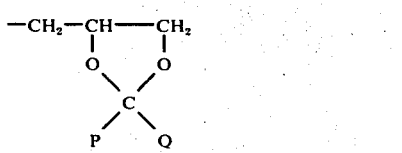

and P and Q have the above definitions to obtain a compound of the formula

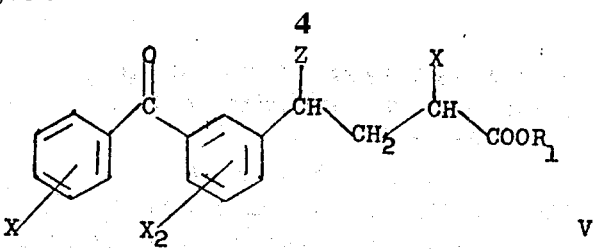

V which can be saponified to the free acid or into an ester by transesterification or esterification or into a salt and when R₁ is

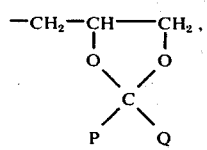

can be subjected to acid hydrolysis to obtain the corresponding 2,3-dihydroxypropyl ester.

In a preferred embodiment of the process, the chlorination agent is thionyl chloride, oxalyl chloride, phosphorus trichloride and phosphorus pentachloride and the rearrangement of the diazoketone of formula IV is effected preferably in the presence of a metal catalyst such as a silver base catalyst, i.e. silver oxide or silver benzoate or simply by heating.

The starting material of formula II can be prepared by methods analogous to those described in French BSM patent No. 8440 M. To obtain a compound of formula II in which Z is hydrogen, an alkyl malonate is reacted with a 3-bromomethyl-benzophenone and the corresponding malonic acid derivative is subjected to acid hydrolysis and a decarboxylation. To obtain a compound of formula II in which Z is alkyl, the desired m-benzoylphenyl-acetonitrile is reacted with an alkylating agent to obtain the corresponding m-benzoyl-α-alkyl-phenyl-acetonitrile and the latter is subjected to acid hydrolysis to form the m-benzoyl-α-alkylphenylacetic acid and the latter is homologated by the Arndt-Eistert method to form the corresponding m-benzoylphenyl-propionic acid.

The m-benzoyl-phenyl-acetic acids can also be prepared and the α-alkyl derivatives thereof by the methods described in French patent No. 1,516,775 and Belgian patent No. 718.466. The esters of m-benzoylphenyl acetic acids can be α-alkylated by reaction with an alkaline agent and then alkyl iodide. The m-benzoylphenyl-acetic acid can be homolgated such as by the Arndt-Eistert method to form the corresponding m-benzoyl-phenyl-propionic acids of formula II. Another method of obtaining compounds of formula II with alkyl substituents on the benzene ring is illustrated in Example IV.

The process for the preparation of compounds of formula Ib comprises reacting an M-benzoyl-phenyl-acetic acid of the formula

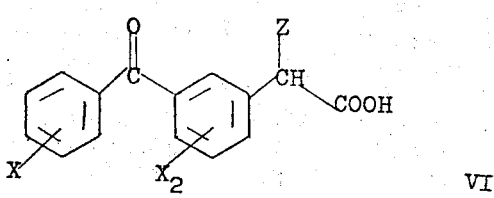

VI wherein X, X₂ and Z are defined as in formula Ib with a chlorinating agent to form the corresponding acid chloride, reacting the latter with a diazoalkane of the formula X₄-CHN₂ wherein X₄ has the above definition to form a diazoketone of the formula

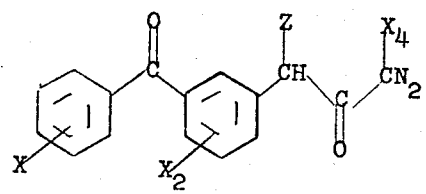

VII reacting the latter with an anhydrous hydrogen halide to form a halomethylketone of the formula

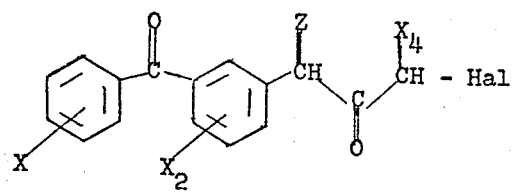

VIII wherein Hal is a halogen, treating the latter with a reducing agent to form a diol of the formula

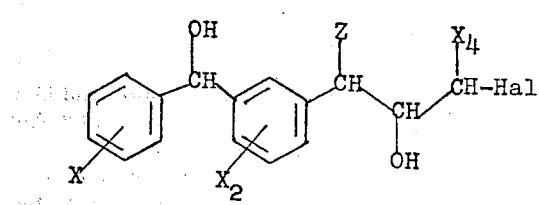

IX reacting the latter with an alkali metal cyanide to form a nitrile of the formula

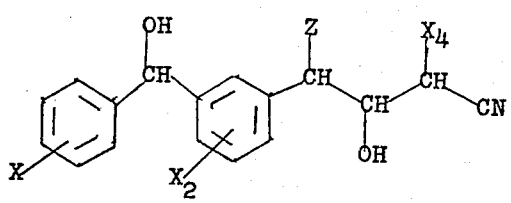

X reacting the latter with a selective oxidizing agent to obtain a compound of the formula

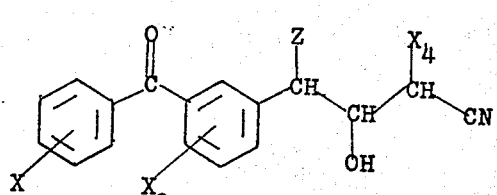

XI reacting the latter with a compound of the formula R₂OH wherein R₂ is selected from the group consisting of hydrogen and alkyl of 1 to 5 carbon atoms to form a compound of the formula

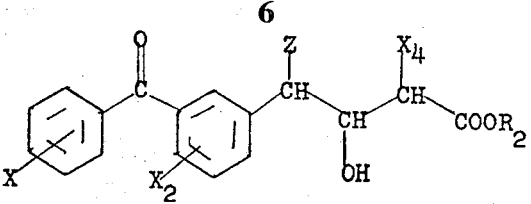

Ib' which, if desired, when R₂ is alkyl of 1 to 5 carbon atoms, is subjected to the action of a dehydrating agent to form a compound of the formula

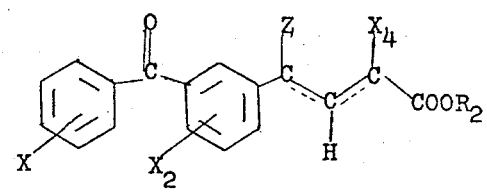

Ib"

with the double bond αβ or βγ to the carboxylic group, separating if necessary the unsaturated αβ and βγ isomers and subjecting if desired the product of formula Ib' and Ib" to a saponification or transesterification when R₂ is alkyl of 1 to 5 carbon atoms or a salification or esterification when R₂ is hydrogen and then when R₂ is 2,3-(P,Q-methylenedioxy)-propyl, the product can be subjected to acid hydrolysis to form the corresponding 2,3-dihydroxypropyl derivative. The compounds of formula Ib when having a double bond can be trans or cis isomeric form.

In preferred embodiments of the process, the chlorination agent may be thionyl chloride, oxalyl chloride, phosphorus trichloride or phosphorus pentachloride; the reducing agent is an aluminum alcoholate, notably aluminum isopropylate or aluminum tert.-butylate; the selective oxidizing agent is manganese dioxide, silver silicate and preferably chromic anhydride; and the dehydrating agent is p-toluene sulfonic acid and preferably phosphoric acid anhydride and may be operated by heating in xylene. The dehydrated products generally occur as a mixture of αβ and βγ isomers which can be separated by known physical methods.

The process for preparation of compounds of formula Ic comprises reacting a compound of the formula

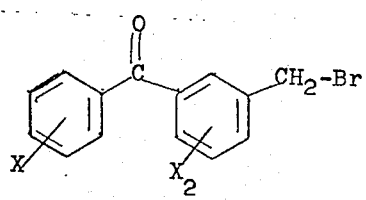

XII with an alkyl acetylacetate of the formula

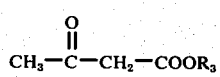

XIII wherein R₃ is alkyl of 1 to 5 carbon atoms to form a compound of the formula

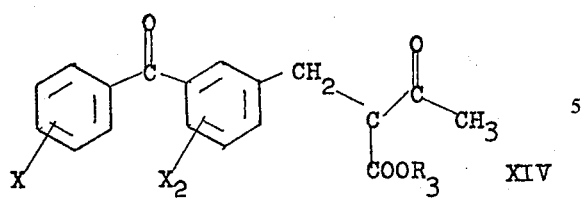

XIV subjecting the latter to hydrolysis and decarboxylation in an acid media to obtain a compound of the formula

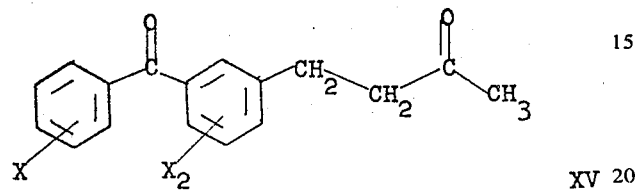

XV and reacting the latter with sulfur and a primary or secondary amine and hydrolyzing the product to obtain a compound of formula Ic wherein R is hydrogen. The said acid can then be salified or esterified and then eventually transesterified to obtain the 2,3-(P,Q-metylenedioxy)-propyl ester which may be acid hydrolyzed to obtain the corresponding 2,3-dihydroxypropyl ester.

In a preferred mode of the process, the hydrolysis and decarboxylation reaction is effected by heating in the presence of an aqueous acid such as hydrochloric acid, sulfuric acid, acetic acid or a mixture of said acids and the amine used for reaction with sulfur is preferably morpholine.

The bromomethyl compounds of formula XII may be prepared by analogous methods to those described in French patent No. 1,546,478 and Belgian patent. No. 718,466.

The novel intermediates of the invention are compounds having a formula selected from the group consisting of

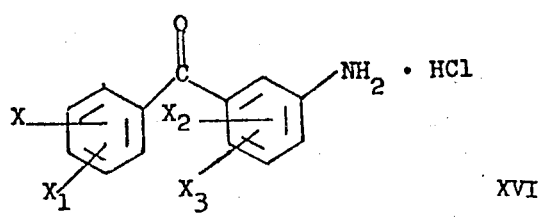

wherein X, $X_2$ and Z have the above definitions and when $A_2$ is $CH_2$—Hal, Hal is a halogen A and $A_1$ are identical and are selected from the group consisting of =O and

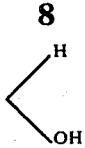

and when $A_2$ is $CH_2$ CN, $A_1$ is

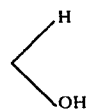

and A is selected from the group consisting of

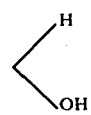

and =O and

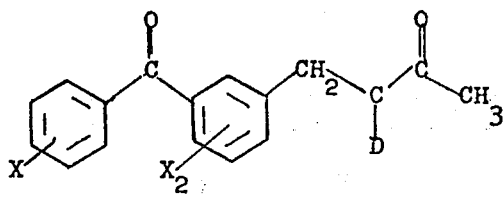

wherein X and $X_2$ have the above definition and D is selected from the group consisting of H and —COOAlk wherein Alk is alkyl of 1 to 5 carbon atoms.

In a variation of the process to produce the compounds of formula I wherein X, $X_1$, $X_2$ and $X_3$ have the above definition and $X_4$, Y, Z and R are hydrogen and a double bond optionally exists $\alpha\beta$ to the carboxylic group and the salts thereof comprises reacting a compound of the formula

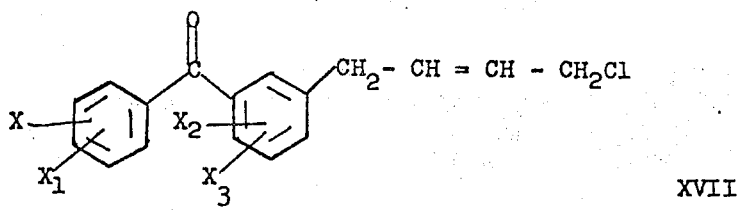

XVI wherein the X's have the above definition with alkali metal nitrite such as sodium nitrite in the presence of a mineral acid such as hydrochloric acid to form the corresponding diazonium salt thereof, reacting the latter with 1,3-butadiene to obtain a 1-chloro-butene-2 of the formula :

reacting the latter with an alkali metal acetate in the presence of acetic acid to obtain the corresponding 1-acetoxybutene-2-compound which is saponified with an alkali metal hydroxide to form the corresponding 1-hydroxy-butene-2-compound and either subjecting the latter to hydrogen in the presence of a metallic catalyst to form the corresponding 1-hydroxy-butane compound which can be oxidized with an oxidizing agent to form the corresponding butyric acid compound which can be salified or oxidizing the latter with an oxidizing agent to obtain the corresponding 2-butenoic acid which may be salified if desired.

This modified process can be used to prepare 4-(3'-p-trifluoromethoxybenzoyl-2'-methyl-phenyl)-butyric acid, 4-(3'-p-fluorobenzoyl-2'-methyl-phenyl)-butyric acid and 4-(3'-p-chlorobenzoyl-2'-methyl-phenyl)-2-butenoic acid.

Another modification of the process comprises reacting 3-bromo-1-propene with methyl 2-hydroxybenzoate to obtain methyl 2'-(3-oxy-1-propene)-benzoate, hydrolyzing the latter to form the free acid, reacting the latter with a chlorinating agent such as thionyl chloride to form the corresponding acid chloride, condensing the latter with cadmium chlorophenyl to form 3-(2'-p-chlorobenzoyl-phenyl)oxy-1-propene, heating the latter to form 3-(3'-p-chlorobenzoyl-2'-hydroxy-phenyl)-1-propene, reacting the latter with an oxidizing atent to form 2-(3'-p-chlorobenzoyl-2'-hydroxy-phenyl)-1-oxo-ethane, condensing the latter with malonic acid, decarboxylating the resulting dicarboxylic acid to form 4-(3'-p-chlorobenzoyl-2'-hydroxy-phenyl)-2-butenoic acid and hydrogenating the latter in the presence of palladium to obtain 4-(3'-p-chlorobenzoyl-2-'-hydroxyphenyl)-butyric acid and finally with an oxidizing agent to form 4-(3'-p-chlorobenzoyl-2',5'-dihydroxyphenyl)-butyric acid.

4-(3'-p-chlorobenzoyl-2'-methyl-phenyl)-butyric acid may be reacted either with an alkoxylation agent such as a methoxylation agent to form 4-(3'-p-alkoxybenzoyl-2'-methyl-phenyl)-butyric acid or with a dialkylamine such as dimethylamine to obtain 4-(3'-dialkylaminobenzoyl-2'-methyl-phenyl)-butyric acid. The 4-(3'-chlorobenzoyl-2'-methyl-phenyl)-butyric acid may also be reacted with a chlorinating agent such as thionyl chloride to form the corresponding acid chloride and the latter may be reacted with salicylic acid to form o-carboxyphenyl 4-(3'-p-chlorobenzoyl-2'-methylphenyl)-butyric acid ester.

4-(m-benzoyl-phenyl)-2-methyl-butyric acid may be reacted with first bromine in the presence of phosphorus bromide and then with methanol to obtain methyl 4-(m-benzoyl-phenyl)-2-methyl-2-bromo-butanoate, subjecting the latter to dehydrobromination to form methyl 4-(m-benzoyl-phenyl)-2-methyl-2-butenoate which is subjected to acid hydrolysis to form 4-(m-benzoyl-phenyl)-2methyl-2-butenoic acid. 4-(m-benzoyl-phenyl)-4-methyl-3-butenoic acid may be hydrogenated in the presence of a metallic catalyst to form 4-(m-benzoyl-phenyl)-4-methyl-butyric acid.

The novel anti-inflammatory and analgesic compositions of the invention which are substantially devoid of ulcerigenic effect are comprised of an effective amount of at least one compound of formula I or its non-toxic, pharmaceutically acceptable salts where appropriate, and a pharmaceutical carrier. The compositions may be in the form of injectable solutions or suspensions in ampoules or multiple dose flacons or in the form of tablets, coated tablets, capsules, syrups, suppositories or pomades prepared in the usual manner.

The compositions are useful for the treatment of rheumatic affections, arthrosis, lombalgies, sciatics, neuralgial, myalgies or toothaches.

The novel method of the invention for the treatment of pain and inflammation in warm-blooded animals comprises administering to warm-blooded animals an effective amount of at least one compound of formula I or its non-toxic, pharmaceutically acceptable salts when R is hydrogen or o-caboxyphenyl. The said compounds may be administered parenterally, orally, rectally or locally by topical application on skin or mucosa. The usual daily dose is 2 to 20 mg/kg depending upon the specific product and the method of administration.

In the following examples there are described several preferred embodiments to illustrate the invention. However, it is to be understood that the invention is not intended to be limited to the specific embodiments.

EXAMPLE I 4-(m-benzoyl-phenyl)-butyric acid

STEP A: ETHYL m-benzoyl benzyl malonate

A mixture of 32 g of 3-methyl-benzophenone (process of Ador et al, Berichte, Vol. 12, p. 2299), 96 ml of carbon tetrachloride, 26 g of N-bromosuccinimide and 100mg of benzoyl peroxide was refluxed for one hour and after the addition of another 100mg of benzoyl peroxide, the mixture was refluxed for 1 hour. Another 100 mg of benzoyl peroxide were added and reflux was maintained for 1½ hours. Another 100 mg of benzoyl peroxide were added and reflux was maintained with stirring for 1½ hours. The mixture was cooled, filtered and the filtrate was distilled to dryness under reduced pressure to obtain 46 g of 3-bromomethyl-benzophenone which was used as is for the next step.

3.84 g of sodium were dissolved with stirring into 100 ml of ethanol and after the addition of 25 ml of ethyl malonate, the mixture was heated to reflux. 46 g of 3-bromomethyl-benzophenone in 46 ml of ethanol were then progressively added thereto and the mixture was then refluxed for 3 hours and concentrated under reduced pressure. 100 ml of water were added thereto and the mixture was extracted with methylene chloride. The organic phase was washed with water and distilled under reduced pressure. The liquid residue was purified by distillation to obtain 16.5 g of ethyl m-benzoyl-benzyl-malonate in the form of a colorless liquid having a boiling point of 216°–218° C at 0.7 mm Hg. The product was soluble in alcohol, chlorinated solvents and benzene and insoluble in water.

Analysis: $C_{12}H_{22}O_5$; molecular weight = 354.41.
Calculated: %C, 71.17; %H, 6.26.
Found: %, 71.5; %H, 6.2.

I.R. Spectrum (chloroform): Presence of C=O at 1730 and $1745^{cm-1}$ and of conjugated ketone at $1661^{cm-1}$.

STEP B: 3-(m-benzoyl-phenyl)-propionic acid

A solution of 16 g of ethyl m-benzoyl-benzyl-malonate, 160 ml of 57% hydroiodic acid and 320 ml of acetic acid was refluxed for 2 hours and then the acetic acid and hydroiodic acid were distilled off. The residue was taken up in water and the aqueous phase was extracted with ethyl acetate. The organic phase was washed with an aqueous sodium chloride solution, dried over magnesium sulfate and distilled to dryness under reduced pressure. The residue was dissolved in a minimum of ether and the solution was filtered through a column of magnesium silicate and eluted with ether. The eluant was distilled to dryness under reduced pressure and the raw product was redissolved in 200 ml of ether. The solution was filtered and after the addition of 4.5 ml of cyclohexylamine, the mixture was iced for 30 minutes and was vacuum filtered. The precipitate was washed with water and dried to obtain 13 g of the cyclohexylamine salt of 3-(m-benzoyl-phenyl)propionic acid melting at 140° C.

The said salt was purified by dissolution in 5 volumes of hot methanol, adding 10 volumes of ethyl acetate, filtering and concentration to 5 volumes while adding ethyl acetate to replace methanol. After icing for 1 hour, the mixture was vacuum filtered and the precipitate was washed with water and dried to obtain 11 g of pure cyclohexylamine salt with an unchanged melting point. The said cyclohexylamine salt was suspended in ethyl acetate and after acidification of the mixture by addition of 20 ml of 2N hydrochloric acid, the mixture was decanted. The organic phase was washed with water, reextracted with ethyl acetate, dried over magnesium sulfate and distilled to dryness under reduced pressure. The residue was taken up in a minimum of ether and the solution was passed through magnesium silicate. The solution was filtered, concentrated to 2 volumes and after the addition of 4 volumes of pentane, the mixture was concentrated while adding pentane until 30 ml of distillate were obtained. Crystallization was started and after icing for 1 hour, the reaction mixture was vacuum filtered. The recovered precipitate was washed with pentane and dried to obtain 5.8 g. of 3-(m-benzoyl-phenyl)-propionic acid melting at 70° C. The product occurred in the form of a colorless solid soluble in chlorinated solvents, alcohols, ethyl acetate, benzene and ether and insoluble in water.

Analysis: $C_{16}H_{14}O_3$; molecular weight = 254.27.
Calculated: %C, 75.57; %H, 5.55.
Found: %C, 75.7, %H, 5.8.

I.R. Spectrum: Presence of acid carbonyl at $1712^{cm-1}$ and conjugated ketone at $1660^{cm-1}$.

STEP C: 3-(m-benzoyl-phenyl)-propionyl chloride

A mixture of 18.15 g of 3-(m-benzoyl-phenyl)-propionic acid and 25 ml of thionyl chloride was refluxed for 1½ hours and excess thionyl chloride was removed under reduced pressure to obtain 3-(m-benzoyl-phenyl)-propionyl chloride which was used as is for the next step.

STEP D: 3-(4'-diazo-3'-oxo-butyl)-benzophenone

A solution of the acid chloride of Step C in 200 ml of methylene chloride was cooled to 0° C and then 400 ml of methylene chloride containing 29.5 g/liter of diazomethane was added thereto at a temperature not greater than 3° C. The mixture was allowed to return to room temperature and was stirred overnight. The methylene chloride was distilled off and the mixture was evaporated to dryness to obtain 3-(4'-diazo-3'-oxobutyl)-benzophenone.

STEP E: 4-(m-benzoyl-phenyl)-butyric acid

A suspension of 24.43 g of silver oxide, 59.37 g of sodium carbonate and 39.01 g of sodium thiosulfate in 270 ml of water was heated to 60° C and the diazoketone of Step D in 126 ml of dioxane was added thereto. The reaction mixture was refluxed for 1½ hours and was then cooled and filtered. The separated aqueous phase was adjusted to a pH of 1 by addition of 60 ml of nitric acid and was extracted with ether. The ether phase was dried over magnesium sulfate and evaporated to dryness under reduced pressure. The residue was purified by crystallization from isopropyl ether to obtain 6.7 g of 4-(m-benzoyl-phenyl)-butyric acid melting at 71° C. The product was soluble in chloroform, methylene chloride, methanol and dilute alkalis and insoluble in water.

Analysis: $C_{17}H_{16}O_3$; molecular weight = 268.31.
Calculated: %C, 76.10; %H, 6.01.
Found: %C, 75.9; %H, 5.9.

RMN Spectrum ($CCl_4$): Aromatic protons −435 to 470 Hz; hydroxyl of carboxyl −599 Hz; hydrogens of aliphatic chain − $C\alpha$ −127, 129 and 139 Hz $C\beta$- 108, 115, 123 and 129 Hz $C\gamma$-154, 161 and 163 Hz.

EXAMPLE II 2,3-isopropylidenedioxypropyl 4-(m-benzoyl-phenyl)-butyrate

STEP A: 3-(4'-diazo-3'-oxo-butyl)-benzophenone

A mixture of 10 g of 3-(m-benzoyl-phenyl)-propionic acid and 50 ml of oxalyl chloride was stirred for 4 hours at room temperature and the excess oxalyl chloride was removed under reduced pressure. The resulting oil was taken up twice in 50 ml of benzene and evaporated to dryness under reduced pressure to obtain 10.7 g of 3-(m-benzoyl-phenyl)-propionyl chloride identical to Example I.

A solution of the said acid chloride in 50 ml of anhydrous methylene chloride was added with stirring in one hour at 0° C to 550 ml of methylene chloride solution containing 8.2 g/liter of diazomethane and after standing overnight, the mixture was allowed to return to 20° C. The mixture was evaporated to dryness under reduced pressure to obtain 11.25 g of 3-(4'-diazo-3'-oxo-butyl)-benzophenone identical to that of Example I.

STEP B: 2,3-isopropylidenedioxypropyl 4-(m-benzoyl-phenyl)-butyrate

A solution of 1 g of silver benzoate in 12.5 ml of triethylamine was added dropwise with stirring to a solution of 11.25 g of the diazoketone of Step A in 80 ml of redistilled and anhydrous 2,2-dimethyl-4-hydroxymethyl-1,3-dioxolane and stirring was continued until nitrogen evolution ceased. Another few drops of the said solution were added until there was no nitrogen evolution and then a pinch of silver benzoate was added to verify that the reacton was complete. The reaction mixture was poured with stirring into 300 ml of water and the mixture was filtered to remove silver salts. The insolubles were washed 4 times with 100 ml of isopropyl ether that was utilized to wash the aqueous phase. The obtained organic phase was washed 4 times with 100 ml of water, dried over sodium sulfate, decolorized with activated carbon, filtered and evaporated to dryness under reduced pressure to obtain 13.05 g of a yellow oil. The oil was purified by chromatography over silica gel and elution with methylene chloride containing 0.1% of triethylamine to obtain 8.18 g 2,3- isopropylidenedioxypropyl 4-(m-benzoyl-phenyl)-butyrate in the form of a yellow oil.

Microanalysis (effected after the product was dried at 150° C)

$C_{23}H_{26}O_5$; molecular weight = 382.44.
Calculated: %C, 72.23; %H, 6.85.
Found: %C, 72.0; %H, 6.9.

I.R. Spectrum: In accordance with the structure, presence of a peak corresponding to ester function at $1739^{cm-1}$.

EXAMPLE III 2,3-dihydroxypropyl 4-(m-benzoyl-phenyl)-butyrate

A mixture of 8.18 g of the ester prepared in Example II, 41 ml of methoxyethanol and 13 g of crystalline boric acid was heated to 100° C with stirring and was stirred for 3 hours at the said temperature and then was iced. The white precipitate formed was eliminated and the mixture was filtered. The filtrate was added to 400 ml of water with stirring and the mixture was washed with ether. The organic phase was washed with 40 ml of a saturated aqueous sodium bicarbonate solution and then was diluted with 400 ml of methylene chloride. The mixture was dried over sodium sulfate, decolorized with activated charcoal, filtered and evaporated to dryness under reduced pressure to obtain 7.5 g of a yellow oil. The oil was purified by chromatography over silica gel and elution with ethyl acetate to obtain 5.56 g of 2,3-dihydroxypropyl 4-(m-benzoyl-phenyl)-butyrate in the form of a colorless oil.

Analysis: $C_{20}H_{22}O_5$; molecular weight = 342.38.
Calculated: %C, 70.16; %H, 6.48.
Found: %C, 70.1; %H, 6.7.

I.R. Spectrum: In accordance with the structure, presence of a peak corresponding to a free hydroxy at $3601^{cm-1}$. Carbonyl: conjugated ketone at 1660 and $1651^{cm-1}$ and ester at $1733^{cm-1}$. Aromatic ring at 1601 - 1584 - $1481^{cm-1}$.

EXAMPLE IV 2,3-isopropylidenedioxypropyl 4-(3'-p-chlorobenzoyl-2'-methylphenyl)-butyrate STEP A: 2-methyl-3-nitro-4'chloro-benzophenone 100 g of 2-methyl-3-nitro-benzoic acid and 500 ml of thionyl chloride were refluxed for 15 hours and the mixture was then evaporated to dryness under reduced pressure to obtain 110 g of 2-methyl-3-nitro-benzoyl chloride which was used as in the synthesis.

A mixture of 30 g of magnesium and 450 ml of ether was refluxed and then a solution of 191 g of p-chloro-bromobenzene in 600 ml of ether was slowly added and reflux was continued for 1½ hours after the addition. The mixture was cooled to 20° C to obtain an ether solution of 0.7N p-chlorophenyl magnesium bromide. After cooling 800 ml of the solution to 10° C, 55.7 g of cadmium chloride were added thereto and the ether was distilled off while adding benzene as a replacement. After obtaining 1 l of distillate, it was cooled to 8° C and a solution of 110 g of 2-methyl-3-nitro-benzoyl chloride in 550 ml of benzene was added thereto. The mixture stood for 18 hours and was then added to a mixture of 3,650 ml of icewater and 134 ml of hydrochloric acid. The mixture was filtered and the benzene phase was decanted. The aqueous phase was extracted with benzene and the combined benzene phases were washed with N hydrochloric acid, with water, with saturated aqueous sodium bicarbonate and finally with water. The organic phase was dried over sodium sulfate and evaporated to dryness under reduced pressure to obtain 147.3 g of 2-methyl-3-nitro-4'-chloro-benzophenone which was used as is in the next step.

For analysis, 13 g of the product were chromatographed over silica gel and eluted with methylene chloride and evaporation of the eluant gave 8.13 g of pure product in the form of a chestnut oil soluble in methylene chloride and ether and insoluble in water.

Analysis: $C_{14}H_{10}ClNO_3$; molecular weight = 275.69.
Calculated: %C, 60.99; %H, 3.65; %Cl, 12.86; %N, 5.08.
Found: %C, 60.0, %H, 4.0; %Cl, 11.4; %N, 5.2.

I.R. Spectrum (chloroform): Presence of conjugated ketone, aromatic and $NO_2$

STEP B: 2-methyl-3-amino-4'-chloro-benzophenone

A mixture of 3,750 ml of hydrochloric acid, 134 g of 2-methyl-3-nitro-4'-chloro-benzophenone and 536 g of stannous chloride was heated at 62° C for 6 hours and was then cooled to 5° C and held therefor 1 hour. The mixture was vacuum filtered and the precipitate was washed with hydrochloric acid and dried under reduced pressure. The residue was stirred for 2 hours at room temperature with 1,300 ml of water, 1,000 ml of 2N sodium hydroxide and 230 ml of ether and the mixture was then extracted with methylene chloride. The organic phase was washed with water, dried over sodium sulfate and evaporated to dryness under reduced pressure to obtain 68.7 g of 2-methyl-3-amino-4'-chloro-benzophenone melting at 65° C which was used as is for the next step.

For analysis, 4.4 g of the raw product were chromatographed over silica gel with elution with a 90:10 methylene chloride-ether mixture and evaporation of the eluant gave 4 g of the product melting at 68° C. The product occurred in the form of beige crystal soluble in methylene chloride and methanol and insoluble in water.

Analysis: $C_{14}H_{12}ClNO$; molecular weight = 245.70.
Calculated: %C, 68.44; %H, 4.92; %Cl, 14.43.
Found: %C, 68.4; %H, 5.0; %Cl, 14.7.

I.R. Spectrum (chloroform): Presence of conjugated ketone at $1660^{cm-1}$, of aromatic and $NH_2$ at 1617 and $1582^{cm-1}$ and of $NH_2$.

STEP C: 3-(3'-p-chlorobenzoyl-2'-methyl-phenyl)-2-chloro-propionic acid

A suspension of 67.5 g of 2-methyl-3-amino-4'-chlorobenzophenone in 250 ml of water had added thereto 88 ml of hydrochloric acid and the mixture was stirred for 20 minutes at 25° to 28° C and was then cooled to 5° C. A solution of 20.4 g of sodium nitrite in 40 ml of water was added thereto and the mixture was stirred for 30 minutes at 5° C and was then vacuum filtered to obtain a solution of 2-methyl-4'-chlorobenzophenone-3-diazonium chloride.

The said solution was then added to a mixture of 340 ml of acetone, 5.4 g of cuprous chloride and 54 ml of acrylic acid heated to 46° C and the mixture was stirred for 30 minutes. After the evolution of 5 liter of nitrogen, the temperature was returned to 20° C and 3,000 ml of methylene chloride was added thereto. The organic phase was washed with water, dried over sodium sulfate and evaporated to dryness under reduced pressure. The residue was dissolved in 800 ml of an aqueous saturated sodium bicarbonate solution and the solution was stirred for 10 minutes, was treated with activated carbon, stirred for another 10 minutes and was vacuum filtered. The pH of the solution was adjusted 1 to 2 by addition of 80 ml of hydrochloric acid with stirring at room temperature and the mixture was extracted with methylene chloride. The organic phase was washed with water, dried over sodium sulfate and evaporated to dryness under reduced pressure to obtain 69 g of 3-(3'-p-chlorobenzoyl-2'-methyl-phenyl)-2-chloropropionic acid which was used as is for the next step.

For analysis, 6.7 g of the raw product was chromatographed over silica gel with a 49-49-2 mixture of benzene-ethyl acetate - methanol as eluant which was evaporated to obtain 2.17 g of the said product in the form of a chestnut amorphous product soluble in methylene chloride.

Analysis: $C_{17}H_{14}Cl_2O_3$; molecular weight = 337.21.
Calculated: %C, 60.55; %H, 4.18; %Cl, 21.03.
Found: %C, 60.6–60.5; %H 4.4–4.3, %Cl, 21.3–20.8.

I.R. Spectrum (chloroform): Presence of acid at $1725^{cm-1}$, conjugated ketone at $1662^{cm-1}$ and of aromatic.

STEP D: 3-(3'-p-chlorobenzoyl-2'-methyl-phenyl)-propionic acid

A mixture of 59 g of 3-(3'-p-chlorobenzoyl-2'-methy-1-phenyl)-2-chloropropionic acid, 472 ml of acetic acid and 118 ml of water was heated to 75° C and after the addition of 23.6 g of zinc, the mixture was held at 75° C for 2½ hours and returned to 20° C. The mixture was vacuum filtered and the reaction mixture was taken up in water and was extracted with methylene chloride. The organic phase was dried over sodium sulfate and was evaporated to dryness under reduced pressure. The residue was chromatographed over silica gel and was eluted with a 75-25 methylene chloride-ether mixture. Evaporation of the eluant gave 3 g of residue which was empasted with 6 ml of isopropyl ether and vacuum filtered. The residue was washed with isopropyl ether and dried under reduced pressure to obtain 1 g of 3-(3'-p-chlorobenzoyl-2'-methyl-phenyl)-propionic acid melting at 144°–148° C which was used as is for the next step.

For analysis, the product was crystallized from isopropyl ether to obtain 570 mg of product in the form of colorless crystals melting at 148° C. The product was soluble in chloroform and insoluble in water.

Analysis: $C_{17}H_{15}ClO_3$; molecular weight = 302.77.
Calculated: %C, 67.44; %H, 4.99; %Cl, 11.71.
Found: %C, 67.7; %H, 4.9; %Cl, 11.4.

I.R. Spectrum (chloroform): Presence of conjugated ketone at $1666^{cm-1}$, aromatic at $1587^{cm-1}$, of carbonyl at $1703^{cm-1}$ and of acid OH at $3494^{cm-1}$.

STEP E: 3-(3'-p-chlorobenzoyl-2'-methyl-phenyl)-propionyl chloride 830 mg of 3-(3'-p-chlorobenzoyl-2'-methyl-phenyl)-propionic acid and 4.2 ml of thionyl chloride were refluxed for 3 hours and then excess thionyl chloride was distilled off and the last traces were removed by entrainment with benzene to obtain 876 mg of 3-(3'-p-chlorobenzoyl-2'-methyl-phenyl)propionyl chloride which was used as is for the next step.

I.R. Spectrum (chloroform): Presence of C=O at $1795^{cm-1}$ and $1663^{cm-1}$ and aromatic.

STEP F: 2,3-isopropylidenedioxypropyl 4-(3'-p-chlorobenzoyl-2'-methyl-phenyl)-butyrate 33 ml of a methylene chloride solution titrating 11 g/liter of diazomethane were added to a solution of 876 mg of 3-(3'-p-chlorobenzoyl-2'-methyl-phenyl)-propionyl chloride in 5 ml of methylene chloride at 5° C and the solution was allowed to stand for 18 hours at room temperature and was then evaporated to dryness under reduced pressure to obtain 975 mg of 3-(4''-diazo-3''-oxo-butyl)-2-methyl-4'-chloro-benzophenone.

I.R. Spectrum (Chloroform): Presence of CH=N$^+$=N$^-$ at $2105^{cm-1}$ of C=O at 1666 and $1661^{cm-1}$, of conjugated ketone at $1643^{cm-1}$ and of aromatic at $1587^{cm-1}$.

A solution of 0.60 g of silver benzoate in 7.5 ml of triethylamine was slowly added to a solution of 920 mg of the said diazoketone in 13 ml of 2,2-dimethyl-4-hydroxymethyl1,3-dioxolane and the mixture was stirred for 15 minutes at room temperature. After evolution of 50 ml of nitrogen, the reaction mixture was poured into water and was extracted with isopropyl ether. The organic phase was washed with water, dried over sodium sulfate and evaporated to dryness under reduced pressure. The residue was chromatographed over silica gel and eluted with a 95:5 methylene chloride-ether mixture. Evaporation of the eluant yielded 525 mg of 2,3-isopropylidenedioxy-propyl 4-(3'-p-chlorobenzoyl-2'-methyl-phenyl)-butyrate in the form of a brown amorphous solid soluble in chloroform and insoluble in water.

Analysis: $C_{24}H_{27}ClO_5$; molecular weight = 430.93.
Calculated: %C 66.88; %H, 6.32; %Cl, 8.23. Found: %C, 66.8, %H, 6.3; %Cl, 7.9.

I.R. Spectrum (chloroform): Presence of ester carbonyl at $1736^{cm-1}$, of conjugated ketone at $1669^{cm-1}$, of aromatic at $1590^{cm-1}$ and of

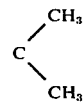

EXAMPLE V

A mixture of 6 g of 2,3-isopropylidenedioxypropyl 4-(3'-p-chlorobenzoyl-2'-methyl-phenyl)-butyrate (Example IV), 60 ml of ethanol, 6 ml of water and 2.3 ml of 12.5N potassium hydroxide was refluxed for 2 hours and the methanol was removed at 50° C at a pressure of 20 mm Hg. The residue was dissolved in 60 ml of water and the solution was treated with activated carbon and filtered. The pH of the filtrate was adjusted to 1–2 by addition of 25 ml of 2N hydrochloric acid and after stirring for 1 hour at 15° C, the mixture was vacuum filtered. The precipitate was washed with water and dried under reduced pressure to obtain 3.7 g of 4-(3'-p-chlorobenzoyl-2'-methyl-phenyl)-butyric acid melting at 124° C. The product occurred in the form of colorless crystals soluble in ethanol, slightly soluble in isopropyl ether and insoluble in water.

Analysis: $C_{18}H_{17}ClO_3$; molecular weight = 316.79.
Calculated: %C, 68.25; %H, 5.41; %Cl, 11.19. Found: %C, 67.9; %H, 5.4; %Cl, 11.3.

I.R. Spectrum (chloroform): Presence of acid dimer carbonyl at $1711^{cm-1}$, of conjugated ketone at $1668^{cm-1}$ and aromatic at $1588^{cm-1}$.

EXAMPLE VI

A mixture of 320 mg of 2,3-isopropylidenedioxypropyl 4-(3'-p-chlorobenzoyl-2'-methyl-phenyl)-butyrate (Example IV), 1.5 ml of methoxy ethanol and 450 mg of boric acid was heated at 100° C for 1 hour 15 minutes and after cooling to 20° C, the mixture was vacuum filtered and the filter was washed with isopropyl ether. The filtrate was added to 10 ml of isopropyl ether and the organic phase was washed with a saturated aqueous solution of sodium bicarbonate and then with water until the wash waters were neutral. The solution was dried over sodium sulfate and evaporated to dryness and the residue was dissolved in 10 ml of methylene chloride. The solution was filtered and evaporated to dryness to obtain 150 mg of 2,3-dihydroxypropyl 4-(3'-p-chlorobenzoyl-2'-methyl-phenyl)-butyrate in the form of a clear yellow amorphous product soluble in chloroform and insoluble in water.

Analysis: $C_{21}H_{23}ClO_5$; molecular weight = 390.87. Calculated: %C, 64.53; %H, 5.93; %Cl, 9.07. Found: %C, 64.5; %H, 6.2; %Cl, 9.3.

I.R. Spectrum (chloroform): Presence of C=O at 1733 and 1669 $cm^{-1}$, of aromatic at 1590 and 1486 $cm^{-1}$, of OH at 3 580 $cm^{-1}$ and of associated OH at 3450 $cm^{-1}$.

EXAMPLE VII 17.5 g of 89% potassium methylate were added under an inert atmosphere to a suspension of 7.5 g of 4-(3'-p-chlorobenzoyl-2'-methyl-phenyl)-butyric acid (Example V) in 75 ml of methanol and was then heated at 120°–130° C for 17 hours under pressure. After cooling to room temperature, the mixture was rinsed with water and the methanol was eliminated under reduced pressure. The residue was dissolved in water, treated hot with activated carbon, iced and filtered. The filtrate was acidified to a pH of 1 with hydrochloric acid and the precipitate formed was recovered by filtration, was washed with water until the wash water was neutral and dried. The residue was crystallized from isopropyl ether to obtain 5.35 g of 4-(3'-p-methoxybenzoyl-2'-methyl-phenyl)-butyric acid in the form of colorless crystals melting at 100° C and then 115° C.

Analysis: $C_{19}H_{20}O_4$; molecular weight= 312.35. Calculated: %C, 73.06; %H, 6.45; %OCH$_3$ 9.93. Found: %C, 73.1; %H, 6.4; %OCH, 10.0.

EXAMPLE VIII

STEP A: 4-(3'-p-chlorobenzoyl-2'-methyl-phenyl)-butyric acid chloride

A mixture of 8 g of 4-(3'-p-chlorobenzoyl-2'-methyl-phenyl)-butyric acid (Example V) and 80 ml of thionyl chloride was refluxed for 45 minutes and after removal of excess thionyl chloride under reduced pressure, 60 ml of benzene were added thereto. The traces of thionyl chloride were removed by entrainment with benzene. This operation was repeated 3 times. The residue was taken up in tetra-hydrofuran to obtain a solution of 4-(3'-p-chlorobenzoyl-2'-methyl-phenyl)-butyric acid chloride which was used as is for the next step.

STEP B: o-carboxy phenyl 4-(3'-p-chlorobenzoyl-2'-methylphenyl)-butyrate

The acid chloride solution from Step A was added with stirring over 40 minutes to a solution of 3.68 g of salicylic acid and 5.36 g of triethylamine in 80 ml of tetrahydrofuran and the mixture was stirred overnight at room temperature. The triethylamine hydrochloride precipitate was removed by filtration and the filtrate was evaporated under reduced pressure. The residue was taken up in water and the solution was extracted with ether. The aqueous phase cooled to 8° C, was acidified by addition of N hydrochloric acid to a pH of 1 and the precipitate formed was extracted with ether (extraction having an insoluble A). The ether phase was washed with water, was dried over magnesium sulfate and evaporated to dryness under reduced pressure. The residue was crystallized from toluene to obtain 0.6 g of o-carboxyphenyl-4-(3'-p-chlorobenzoyl-2'-methyl-phenyl)-butyrate melting at 165° C. Insoluble A was taken up in chloroform and the organic phase was washed with water, dried over magnesium sulfate and evaporated to dryness under reduced pressure. The residue was cristallized from toluene to obtain 1.5 g of the desired product for a total yield of 2.1 g in the form of colorless crystals melting at 165° C.

Analysis: $C_{25}H_{21}ClO_5$; molecular weight = 436.87. Calculated: %C, 68.72; %H, 4.84; %Cl, 8.12. Found: %C, 68.7; %H, 5.0; %Cl, 8.2.

EXAMPLE IX

STEP A: 3-(4'-diazo-3'-oxo-pentyl)-benzophenone

Using the procedure of Step A of Example II, 22.98 g of 3-(m-benzoyl-phenyl)-propionic acid and 115 ml of oxalyl chloride were reacted to obtain 24.59 g of 3-(m-benzoyl phenyl)-propionyl chloride. A solution of the said acid chloride in 50 ml of anhydrous ether was added with stirring at 25° C in 45 minutes to 1,460 ml an ether solution of 10.5 g/liter of diazomethane and the mixture was stirred at 25° C for 16 hours and then evaporated to dryness under reduced pressure to obtain 29 g of raw product which was purified by chromatography over silica with a 95-5 methylene chloride-ethyl acetate eluant which was evaporated to dryness to obtain 19 g of 3-(4'-diazo-3'-oxo-pentyl)-benzophenone. STEP B: 2,3-isopropylidenedioxypropyl 4-(m-benzoyl-phenyl)-2-methyl-butyrate A solution of 19 g of the diazoketone from Step A in 190 ml of redistilled 2,2-dimethyl-4-hydroxymethyl-1,3- dioxolane was heated with stirring at 170° C on a metallic bath and after the evolution of gas ceased, the mixture was cooled to 20° C and poured with agitation into 1 liter of water. The mixture was extracted 3 times with 250 ml of isopropyl ether and the organic phase was washed 3 times with 150 ml of water, dried over sodium sulfate; decolorized with activated carbon, filtered and evaporated to dryness under reduced pressure to obtain 25.4 g of an orange oil. The oil was purified by chromatography over silica and elution with methylene chloride. Evaporation of the eluant to dryness gave 9.07 g of 2,3-isopropylidenedioxypropyl 4-(m-benzoyl-phenyl)-2-methylbutyrate in the form of a yellow oil.

Analysis: $C_{24}H_{28}O_5$; molecular weight = 396.46. Calculated: %C, 72.7; %H, 7.12. Found: %C, 72.9; %H, 6.8.

I.R. Spectrum: in accordance with the structure. Presence of bands in the aromatic region at 1591 and 1582 $cm^{-1}$, conjugated carbonyl at 1650 $cm^{-1}$, ester carbonyl at 1733 $cm^{-1}$, presence of ketal.

RMN Spectrum: Signals corresponding to aromatic protons between 430 and 470 Hz, methylene-α-to aromatic ring: signals at 154, 161, 169 Hz Ch - α - to CO signals between 130 and 170 Hz, Methyl α to carboxyl: signal at 69 and 75.5 Hz,

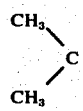

signal at 80.5 to 84.5 Hz, CH$_2$—CH—CH$_2$ signal of 210 to 260 Hz.

EXAMPLE X

A mixture of 3.22 g of 2,3-isopropylidenedioxypropyl 4-(m-benzoyl-phenyl)-2-methyl-butyrate (Step B of Example IX), 16 ml of methoxyethanol and 4.95 g of crystalline boric acid was heated with stirring to 100° C and held with stirring at 100° C for 2 hours. After cooling to 5° C, the insolubles were removed by filtration and the filter was washed with ether. The filtrate was added with stirring to a 160 ml of water at 20° C and the oil formed was extracted 3 times with 30 ml of ether. The ether solution was washed with 30 ml of an aqueous saturated sodium chloride solution and the organic phase was diluted with 100 ml of methylene chloride, dried over sodium sulfate, decolorized with activated carbon, filtered and evaporated to dryness under reduced pressure to obtain 2.79 g of 2,3-dihydroxypropyl 4-(m-benzoyl-phenyl)-2methyl-butyrate in the form of an orange oil.

Analysis: $C_{21}H_{24}O_5$; molecular weight = 356.40. Calculated: %C, 70.76; %H, 6.79. Found: %C, 70.5; %H, 6.7.

I.R. Spectrum: in accordance with structure.
Ester function: peak at $1733^{cm-1}$.
Conjugated ketone: band at 1661 and $1653^{cm-1}$.
Bands in aromatic region at 1601 and $1584^{cm-1}$, hydroxyl band at 3601 and $3494_{cm^{-1}}$.

EXAMPLE XI

A mixture of 4.39 g of 2,3-isopropylidenedioxypropyl 4-(m-benzoyl-phenyl)-2-methyl-butyrate (Step B of Example IX), 44 ml of ethanol, 4.4 ml of water and 1.75 ml of concentrated potassium hydroxide aqueous solution was stirred at reflux for 1 hour and then was evaporated to dryness under reduced pressure. The residue was dissolved in 50 ml of water and the solution was treated with activated carbon, filtered, and acidified with agitation at 20° C to a pH of 1 by addition of 18 ml of 2N hydrochloric acid. The oil formed was extracted 3 times with 20 ml of methylene chloride and the methylene chloride phase was washed twice with 20 ml of water until just neutral. The solution was dried over sodium sulfate, decolorized with activated carbon, filtered and evaporated to dryness under reduced pressure to obtain 3.02 g of an orange oil. The oil was purified by chromatography over silica with elution with 80-20-0.3 mixture of methylene chloride-acetone-acetic acid and after treatment with activated carbon, filtration and evaporation to dryness, 2.37 g of 4-(m-benzoyl-phenyl)-2-methyl-butyric acid were obtained as an orange oil.

Analysis: $C_{18}H_{28}O_3$; molecular weight = 282.32. Calculated: %C, 76.57; %H, 6.43. Found: %C, 76.3; %H, 6.4.

I.R. Spectrum: Presence of acid at 1743 and $1710^{cm-1}$, free hydroxyl peak at $3488^{cm-1}$ and associated hydroxy; conjugated ketone peak at $1660^{cm-1}$, and bands at aromatic region at 1600 and $1582^{cm-1}$.

RMN Spectrum:
$CH_3$—CH— signal at 70 and 76.5 Hz.
Methylene central in a chain: signals at 90 to 130 Hz.
Methylene α to phenyl and CH; signal at 130 to 185 Hz.
Aromatic protons: signal at 440 to 475 Hz.
Mobile hydrogen at 570 Hz

EXAMPLE XII

STEP A: METHYL 4-(m-benzoyl-phenyl)-2-methyl-2-bromo-butanoate 0.2 ml of bromine was added in 10 minutes at room temperature to a suspension of 500 mg of 4-(m-benzoyl-phenyl)-2-methyl-butyric acid and 0.17 ml of phosphorus bromide and the mixture was heated at 52° C for 18 hours and was then cooled to 20° C. 0.8 ml of methanol were added thereto over 15 minutes and the mixture was refluxed for 10 minutes and cooled to room temperature. A solution of 32 mg of sodium sulfite in 2.4 ml of water was added to the reaction mixture which was then extracted with methylene chloride. The organic phase was washed with water until the wash water was neutral, dried over sodium sulfate, treated with activated carbon, filtered and evaporated to dryness under reduced pressure. The residue was chromatographed over silica gel and eluted with a 50-50 methylene chloride-hexane mixture to obtain 326 mg of methyl 4-(m-benzoyl-phenyl)-2-methyl-2-bromo-butanoate in the form of an oil.

Analysis: $C_{19}H_{19}BrO_3$; molecular weight = 375.27. Calculated: %C, 60.81; %H, 5.10; %Br, 21.30. Found: %C, 60.6; %H, 5.1; %Br, 21.6.

STEP B: METHYL 4-(m-benzoyl-phenyl)-2-methyl-2-butenoate

A mixture of 1.46 g of methyl 4-(m-benzoyl-phenyl)-2-methyl-2-bromo-butanoate and 7.3 ml of quinoline was heated at 160° C for 3 hours and after cooling to room temperature, 73 ml of 2N hydrochloric acid were added thereto. The mixture was extracted with methylene chloride and the organic phase was washed with 2N hydrochloric acid, with aqueous saturated sodium bicarbonate solution and then with water. The solution was dried over sodium sulfate, treated with activated carbon, filtered and evaporated to dryness under reduced pressure. The residue was chromatographed over magnesium silicate and eluted with methylene chloride to obtain 615 mg of methyl 4-(m-benzoyl-phenyl)-2-methyl-2-butenoate in the form of an oil.

Analysis: $C_{19}H_{18}O_3$; molecular weight = 294.33. Calculated: %C, 77.53; %H, 6.16. Found: %C, 77.6; %H, 6.2.

STEP C: 4-(m-benzoyl-phenyl)-2-methyl-2-butenoic acid

A mixture of 615 mg of methyl 4-(m-benzoyl-phenyl)-2-methyl-2-butenoate, 6.2 ml of ethanol, 0.6 ml of water and 0.4 ml of a concentrated aqueous solution of potassium hydroxide was refluxed for 1 hour and then was evaporated to dryness under reduced pressure. The residue was taken up in water and the solution was treated with activated carbon, filtered and acidified to a pH of 1 with 2 N hydrochloric acid. The solution was extracted with methylene chloride and the organic phase was washed with water, dried over sodium sulfate, treated with activated carbon, filtered and evaporated to dryness under reduced pressure. The residue was chromatographed over silica gel with 90-10 ether-methylene chloride eluant to obtain 287 mg of 4-(m-benzoyl-phenyl)-2-methyl-2-butenoic acid in the form of an oil.

Analysis: $C_{18}H_{16}O_3$; molecular weight = 180.31. Calculated: %C, 77.12; %H, 5.75. Found: %C, 77.2; %H, 5.7.

EXAMPLE XIII

STEP A: ETHYL 3-(p-chlorobenzoyl)-benzyl malonate

A solution of 28 g of ethyl malonate in 28 ml of dimethylformamide was added to a suspension of 8.4 g of sodium hydride in 260 ml of dimethylformamide at a temperature of 10° to 15° C and the temperature was allowed to return to room temperature. After evolution of 3.9 liters of hydrogen, the resulting solution was poured into a suspension of 52.5 g of 3-bromomethyl-4'-chlorobenzophenone (French BSM No. 8440 M) in 400 ml of dimethylformamide at 24° C. The mixture was stirred for 2 hours and was then evaporated to dryness under reduced pressure. The residue was taken up in 500 ml of water and 75 ml of isopropyl ether and the organic phase was decanted. The aqueous phase was extracted with isopropyl ether and the combined organic phases were dried over sodium sulfate, treated with activated carbon, filtered and evaporated to dryness under reduced pressure. The residue was dissolved in 63 ml of isopropyl ether with agitation, was iced and crystallization was started. After being iced overnight, the mixture was vacuum filtered and the precipitate was washed with isopropyl ether. The mother liquors were evaporated to dryness to obtain 48.7 g of ethyl 3-(p-chlorobenzoyl)-benzyl malonate which was used as is for the next step.

For analysis, 795 mg of the raw product were chromatographed over silica gel with elution with a 96-4 benzeneethyl acetate mixture which after evaporation gave 450 mg of pure product.

Analysis: $C_{21}H_{21}ClO_5$; — molecular weight = 388.85. Calculated: %C, 64.87; %H, 5.44; %Cl, 9.12. Found: %C, 65.1–65.1; %H, 5.3–5.2; %Cl, 10.1–10.2.

I.R. Spectrum (chloroform): Presence of conjugated ketone at $1661^{cm-1}$, of carbonyl at 1729 and $1745^{cm-1}$ and of aromatic.

STEP B: 3-(3'-p-chlorobenzoyl-phenyl)-propionic acid

A solution of 15.2 g of ethyl 3-(p-chlorobenzoyl)-benzyl malonate in 50 ml of acetic acid was added to a solution of 50 ml of sulfuric acid and 50 ml of water and the mixture was refluxed under a nitrogen atmosphere for 20 hours and then cooled to room temperature. The mixture was poured into water and then extracted with methylene chloride. The organic phase was extracted with N sodium hydroxide and the alkaline phase was treated with activated carbon, filtered and acidified by addition at 10° C with stirring of 270 ml of N hydrochloric acid. The mixture was vacuulm filtered and the precipitate was washed with water and dried under reduced pressure to obtain 3.11 g of 3-(3'-p-chlorobenzyl-phenyl)-propionic acid which was used as is for the next step.

For analysis, 5 g of the raw product were dissolved in 15 ml of refluxing acetone and the solution was filtered hot and then was iced for 30 minutes and was vacuum filtered. The precipitate was washed with water and dried under reduced pressure to obtain 3.2 g of the pure product melting at 140° C. The product occurred in the form of a colorless solid soluble in chloroform and methylene chloride and insoluble in water.

Analysis: $C_{16}H_{13}ClO_3$; molecular weight = 288.74. Calculated: %C, 66.56; %H, 4.54; %Cl, 12.28. Found: %C, 66.4; %H, 4.6; %Cl, 12.5.

I.R. Spectrum (chloroform): Presence of dimeric acid carbonyl at $1712^{cm-1}$, of ketone at $1661^{cm-1}$ and of aromatic at 1601, 1586 and $1484^{cm-1}$.

STEP C: 3-(4''-diazo-3''-oxo-butyl)-4'-chloro-benzophenone 6.96 g of 3-(3'-p-chlorobenzoyl-phenyl)-propionic acid and 70 ml of thionyl chloride were refluxed for 3 hours and then evaporated to dryness. The residue was taken up in 100 ml of benzene and evaporated to dryness to obtain 8.7 g of 3-(3'-p-chlorobenzoyl-phenyl)-propionyl chloride which was used as is.

190 ml of a methylene chloride solution of 13.25 g/liter of diazomethane was added to a solution of 8.7 g of the said acid chloride in 50 ml of methylene chloride cooled to 10° C and the mixture was stirred overnight at room temperature and then evaporated to dryness to obtain 8 g of 3-(4''-diazo-3''-oxo-butyl)-4'-chloro-benzophenone which was used as is for the next step.

STEP D: 2,3-isopropylidenedioxypropyl 4-(3'-p-chlorobenzoyl-thenyl)-butyrate 7 ml of a solution of 1 g of silver benzoate in 12.6 ml of triethylamine were added dropwise with stirring at room temperature to a solution of 8 g of the said diazoketone in 50 ml of 2,2-dimethyl-4-hydroxymethyl-1,3-dioxolane and after the evolution of 460 ml of nitrogen, the mixture was poured into water and filtered. The aqueous phase was extracted with isopropyl ether and the organic phase was washed with water, dried over sodium sulfate, treated with activated carbon, filtered and evaporated to dryness. The residue was chromatographed over magnesium silicate and was eluted with a 50-50 petroleum ether-mixture which upon evaporation of the eluant gave 5 g of 2,3-isopropylidenedioxypropyl 4-(3'-p-chlorobenzoyl-phenyl)-butyrate.

For analysis, the residue was dissolved in 40 ml of isopropyl ether and the solution was treated with activated carbon, filtered and evaporated to dryness to obtain 3.78 g of pure product in the form of a yellow oil soluble in chloroform and methylene chloride and insoluble in water.

Analysis: $C_{23}H_{25}ClO_5$; molecular weight = 416.90. Calculated: %C, 66.26; %H, 6.05; %Cl, 8.50. Found: %C, 66.1; %H, 5.9; %Cl, 9.1-9.1.

EXAMPLE XIV 2.4 g of 2,3-isopropylidenedioxypropyl 4-(3'-p-chlorobenzoyl-phenyl)-butyrate (Example XIII), 12 ml of methoxyethanol and 3.5 g of boric acid was heated at 100° C for 23 hours and the mixture was then iced and filtered. The filtrate was added to water with agitation and was extracted with ether. The ether phAse was washed with an aqueous saturated sodium chloride solution and then 40 ml of methylene chloride were added thereto. The organic phase was dried over sodium sulfate, treated with activated carbon, filtered and evaporated to dryness under reduced pressure. The residue was chromatographed over magnesium silicate and eluted with ether. The elute was evaporated to dryness and the residue was dissolved in 20 ml of methylene chloride. The solution was filtered and evaporated to dryness to obtain 1.1 g of 2,3-dihydroxypropyl 4-(3'-p-chlorobenzoyl-phenyl)-butyrate in the form of a yellow oil soluble in chloroform, acetone and ether and insoluble in water.

Analysis: $C_{20}H_{21}ClO_5$; molecular weight = 376.84. Calculated: %C, 63,74; %H, 5.62; %Cl, 9.41. Found: %C, 63.9; %H, 5.8; %Cl, 9.8.

I.R. Spectrum (chloroform): Presence of ester carbonyl at $1729^{cm-1}$, of conjugated ketone at $1658^{cm-1}$, of aromatic at $1582^{cm-1}$ and of OH

EXAMPLE XV

A mixture of 3.9 g of 2,3-isopropylidenedioxypropyl 4-(3'-p-chlorobenzoyl-phenyl)-butyrate, 39 ml of ethanol, 3.9 ml of water and 1.5 ml of 12.5N potassium hydroxide was refluxed for 1½ hours and then was evaporated to dryness. The residue was dissolved in 30 ml of water and the solution was treated with activated carbon and filtered. The filtrate was acidified by addition of 12 ml of 2N hydrochloric acid with agitation and the mixture was vacuum filtered. The precipitate was washed with water until the wash water was neutral and dried under reduced pressure. The residue was dissolved in 30 ml of a saturated aqueous sodium bicarbonate solution and the solution was treated with activated carbon, filtered and acidified by addition of 20 ml of 2N hydrochloric acid. The mixture was vacuum filtered and the precipitate was washed with water until the wash water was neutral and dried under reduced pressure. The residue was empasted with stirring with 10 ml of isopropyl ether and the mixture stood for 1 hour. The residue was washed with isopropyl ether and dried under reduced pressure. The residue was chromatographed over silica gel and eluted with a 50–50 chloroform-acetone mixture which was evaporated under reduced pressure to obtain 1.3 g of 4-(3'-p-chlorobenzoyl-phenyl)-butyric acid melting at 94° C. The product occurred in the form of a colorless solid soluble in benzene, chloroform and acetone and insoluble in water.

Analysis: $C_{17}H_{15}ClO_3$; molecular weight = 302.77. Calculated: %C, 67.44; %H, 4.99; %Cl, 11.71. Found: %C, 67.6; %H, 5.1; %Cl, 11.8.

I.R. Spectrum(chloroform): Presence of acid: dimeric carbonyl at $1709^{cm-1}$, of conjugated ketone at $1659^{cm-1}$, and of aromatic at 1600, 1586, 1568 and $1749^{cm-1}$.

EXAMPLE XVI

STEP A: 3-(3'-chloro-2'-oxo-propyl)-benzophenone 20 g of m-benzoyl-phenyl acetic acid (prepared by process of French patent No. 1,546,478) and 100 ml of thionyl chloride were refluxed for 3 hours and then evaporated to dryness. Excess thionyl chloride was removed by entrainment with benzene to obtain 21.74 g of m-benzoyl-phenyl-acetic acid chloride.

A solution of 21.74 g of the said acid chloride in 40 ml of methylene chloride was added to 570 ml of a solution of methylene chloride titrating 18.7 g/liter of diazomethane at 5° C and the mixture was stirred overnight to obtain a methylene chloride solution of 3-(3'-diazo-2'-oxo-propyl)benzophenone. A current of hydrochloric gas was passed through the said solution for 2 hours at room temperature and the methylene chloride solution was washed with water, then with an aqueous saturated sodium bicarbonate solution and finally water. The said solution was dried over sodium sulfate, treated with activated carbon, filtered and evaporated to dryness. The residue was dissolved in 50 ml of methylene chloride and the solution was passed through a magnesium silicate column and evaporated to dryness. The residue was empasted with 20 ml of isopropyl ether for 10 minutes and was vacuum filtered, washed with isopropyl ether and dried under reduced pressure to obtain 17.31 g of 3-(3'-chloro-2'-oxo-propyl)-benzophenone which was used as is for the next step.

For analysis, 840 mg of the residue were chromatographed over silica gel and were eluted with a 25–75 ethyl ether-petroleum ether mixture which was evaporated to dryness. The residue was empasted with isopropyl ether and dried under reduced pressure to obtain 630 mg of pure product melting at 64° C. The product was in the form of a colorless solid soluble in chloroform and insoluble in water.

Analysis: $C_{16}H_{13}ClO_2$; molecular weight = 272.74. Calculated: %C, 70.46; %H, 4.81; %Cl, 13.00. Found: %C, 70.3; %H, 4.8; %Cl, 13.0.

I.R. Spectrum (chloroform): Presence of CO at $1733^{cm-1}$ and of CO and aromatic at 1661, 1601, 1588 and $1582^{cm-1}$.

STEP B: 3-(3'-chloro-2'-hydroxypropyl)-benzhydrol

A solution of 11.23 g of 3'(3'-chloro-2'-oxo-propyl)-benzophenone in 112 ml of isopropanol was added to 50 ml of isopropanol and 17 g of aluminum isopropylate heated to 50° C and the mixture was refluxed for 2 hours while slowly distilling isopropanol and the acetone formed while keeping the volume constant by adding 30 ml of isopropanol. The mixture was concentrated to 50 ml and after returning to room temperature, the mixture was added with stirring to a mixture of ice-water-hydrochloride acide. The mixture was extracted with methylene chloride and the organic phase was washed with water, dried over sodium sulfate, treated with activated carbon, filtered and evaporated to dryness to obtain 11.97 g of 3-(3'-chloro-2'-hydroxypropyl)-benzhydrol which was used as is for the next step.

For analysis, 1 g of the residue was chromatographed over magnesium silicate and was eluted with methylene chloride which as evaporated to obtain 242 mg of pure product melting at 65° C. The product was a colorless solid soluble in chloroform.

Analysis: $C_{16}H_{17}ClO_2$; molecular weight = 276.77. Calculated: %C, 69.44; %H, 6.19; %Cl, 12.81. Found: %C, 69.3; %H, 6.3; %Cl, 13.0.

I.R. Spectrum (chloroform): Presence of OH at $3588^{cm-1}$ and aromatic.

STEP C: 3-(3'-cyano-2'-hydroxypropyl)-benzhydrol

A mixture of 11.97 g of 3-(3'-chloro-2'-hydroxypropyl)-benzhydrol, 120 ml of ethanol, 2.4 ml of water and 2.66 g of potassium cyanide was refluxed for 3 hours and then evaporated to dryness. The residue was taken up in 200 ml of methylene chloride and the organic phase was washed with water, dried over sodium sulfate, treated with activated carbon, filtered and evaporated to dryness. The residue was chromatographed over silica and was eluted with a 75–25 methylene chloride-ethyl acetate mixture which was evaporated to obtain 7.8 g of 3-(3'-cyano-2'-hydroxypropyl)-benzhydrol in the form of an orange amorphous solid soluble in chloroform and insoluble in water.

Analysis: $C_{17}H_{17}NO_2$; molecular weight = 267.31. Calculated: %C, 76.38; %H, 6.41; %N, 5.24. Found: %C, 76.2; %H, 6.3; %N, 4.9.

I.R. Spectrum (chloroform): Presence of C≡N, free and associated OH and aromatic.

STEP D: 3-(3'-cyano-2'-hydroxypropyl)-benzophenone 7.35 ml of a sulfochromic mixture titrating 26.5 g of chromic anhydride per 100 ml was added with stirring at 0° C to 7.8 g of 3-(3'-cyano-2'-hydroxypropyl)-benzhydrol in 78 ml of acetone and the mixture was allowed to stand at 0° C for 5 minutes and was then poured into water with stirring. The mixture was extracted with methylene chloride and the organic phase was washed with water, dried over sodium sulfate, treated with activated carbon, filtered and evaporated to dryness to obtain 7.4 g of 3-(3'-cyano-2'-hydroxypropyl)-benzophenone which was used as is for the next step.

I.R. Spectrum (chloroform): Presence of cyano at $2252^{cm-1}$, of OH at $3601^{cm-1}$, of CO at $1660^{cm-1}$ and of aromatic at 1600, 1584 and $1482^{cm-1}$.

STEP E: ETHYL 4-(m-benzoyl-phenyl)-3-hydroxybutyrate

A current of hydrochloric acid gas was passed through a solution of 7.4 g of 3-(3'-cyano-2'-hydroxypropyl)-benzophenone in 74 ml of ethanol for 1 hour at room temperature and the mixture was refluxed for 1 hour and then the ethanol was removed at 50° C. The residue was taken up in 200 ml of methylene chloride and the organic phase was washed with water, then an aqueous sodium bicarbonate solution and finally with water. The solution was dried over sodium sulfate, treated with activated carbon, filtered and evaporated to dryness to obtain 7.62 g of ethyl 4(-m-benzoyl-phenyl)-3-hydroxy-butyrate.

For analysis, the residue was chromatographed over silica and was eluted with a 95–5 mixture of methylene chloride-acetone which was evaporated to obtain 5.5 g of pure product in the form a yellow amorphous solid soluble in chloroform and ethanol and insoluble in water.

Analysis: $C_{19}H_{20}O_4$; molecular weight = 312.35. Calculated: %C, 73.06; %H, 6.45. Found: %C, 72.8; %H, 6.3.

I.R. Spectrum (chloroform): Presence of aromatic at 1600, 1582 and $1477^{cm-1}$, of ester CO at $1721^{cm-1}$, of conjugated ketone at 1660 and $1652^{cm-1}$ and of complex OH at $3590^{cm-1}$. Absence of C≡N.

EXAMPLE XVII 2.7 ml of water and 1.4 ml of 12.5N potassium hydroxide were added to a solution of 2.7 g of ethyl 4-(m-benzoylphenyl)-3-hydroxy-butyrate in 27 ml of ethanol and the mixture was refluxed for 1½ hours and then evaporated to dryness. The residue as taken up in 27 ml of water and the solution was treated with activated carbon, filtered and acidified to a pH of 1 by adding 10 ml of 2N hydrochloric acid with stirring at 10° C. The mixture was extracted with methylene chloride and the organic phase was washed with water, dried over sodium sulfate, treated with activated carbon, filtered and evaporated to dryness to obtain 2.36 g of 4-(m-benzoyl-phenyl)-3-hydroxy-butyric acid in the form of a colorless amorphous solid soluble in chloroform and insoluble in water.

Analysis: $C_{17}H_{16}O_4$; molecular weight = 284.30. Calculated: %C, 71.82; %H, 5.67. Found: %C, 71.6; %H, 5.8.

I.R. Spectrum (chloroform): Presence of OH at $3589^{cm-1}$, of acid at $1710^{cm-1}$, of conjugated ketone at $1658^{cm-1}$ and of aromatic at 1601 and $1582^{cm-1}$.

EXAMPLE XVIII 315 mg of phosphoric anhydride were added to a solution of 1.12 g of ethyl 4-(m-benzoyl-phenyl)-3-hydroxybutyrate in 20 ml of xylene and the mixture was refluxed for 2 hours and then cooled to room temperature. The organic phase was washed with water, then with an aqueous saturated sodium bicarbonate solution and then water, dried over sodium sulfate, treated with activated carbon, filtered and evaporated to dryness under reduced pressure. The residue was chromatographed over silica gel and was eluted with methylene chloride which was evaporated to dryness to obtain ethyl 4-(m-benzoylphenyl)-3-butenoate whose ultraviolet spectrum was in accord with the structure.

A mixture of 275 mg of ethyl 4-(m-benzoyl-phenyl)-3-butenoate, 2.75 ml of ethanol, 0.275 ml of ethanol, 0.275 ml of water and 0.08 ml of 12.5N potassium hydroxide was refluxed for 30 minutes and then was evaporated to dryness. The residue was dissolved in 10 ml of water and the solution was treated with activated carbon, and filtered. 3 ml of N hydrochloric acid were added thereto and the mixture was extracted with methylene chloride. The organic phase was washed with water, dried over sodium sulfate, treated with activated carbon, filtered and evaporated to dryness under reduced pressure to obtain 166 mg of 4-(m-benzoyl-phenyl)-3-butenoic acid in the form of a yellow oil soluble in chloroform and ethanol and insoluble in water.

Analysis: $C_{17}H_{14}O_3$; molecular weight = 266.28. Calculated: %C, 76.67; %H, 5.30. Found: %C, 76.4; %H, 5.6.

EXAMPLE XIX

STEP A: 2-(m-benzoyl-phenyl)-propionic acid 1300 ml of a methylene chloride solution titrating 12.5 g/liter of diazomethane was added progressively at 10°–15° C to a solution of 50 g of m-benzoyl-phenyl acetic acid in 500 ml of methylene chloride and after stirring for 15 minutes, excess diazomethane was destroyed by the addition of acetic acid. The organic solution was washed with an aqueous saturated sodium bicarbonate solution and then with water and evaporated to dryness under reduced pressure to obtain 52.5 g of methyl m-benzoyl-phenyl-acetate which was used as is for the α-alkylation step.

138 ml of a solution of 1.55N butyl lithium in hexane was introduced over 20 minutes at −40° C to a mixture of 775 ml of tetrahydrofuran, 775 ml of hexamethyl phosphor-triamide and 21.5 ml of diethylamine and after stirring for 20 minutes, a solution of 52.5 g of the above ester in 470 ml of tetrahydrofuran was added over 20 minutes. Then, 38 ml of methyl iodide were added thereto and the mixture was stirred for 30 minutes at about −40° C and then was progressively returned to 20° C. The reaction mixture was poured into 3 liters of water-ice mixture and was stirred and extracted with isopropyl ether. The extracts were washed with water and evaporated to dryness under reduced pressure to obtain methyl 2-(m-benzoyl-phenyl)-propionate which was used as is for the saponification.

A mixture of 57 g of the said methyl ester, 570 ml of ethanol, 57 ml of water and 29.5 ml of 14N potassium hydroxide was refluxed for 1 hour and the ethanol was distilled under reduced pressure. The residue as dissolved in 600 ml of water and the solution was acidified to a pH of 1 by addition of concentrated hydrochloric acid. The mixture was extracted with methylene chloride and the extracts were washed with water and evaporated to dryness under reduced pressure. The residue was crystallized from isopropyl ether to obtain 31.2 g of 2-(m-benzoyl-phenyl)-propionic acid melting at 82°–83° C.

Analysis: $C_{16}H_{14}O_3$; molecular weight = 254.27. Calculated: %C, 75.57; %H, 5.55. Found: %C, 75.3; %H, 5.7.

The IR and RMN spectra were in accord with the structure.

STEP B: 3-(1'-methyl-2'-oxo-3'-chloropropyl)-benzophenone

Using the procedure of Step A of Example XVI, 2-(m-benzoyl-phenyl)-propionic acid was converted into its acid chloride, then 3-(1'-methyl-2'-oxo-3'-diazopropyl)-benzophenone and finally 3-(1'-methyl-2'-oxo-3'-chloropropyl)-benzophenone which was purified by chromatography over silica gel and was eluted with methylene chloride to obtain the product melting at 60° C.

Microanalysis: $C_{17}H_{15}ClO_2$; molecular weight = 286.76. Calculated: %C, 71.20; %H, 5.27; %Cl, 12.36. Found: %C, 71.5; %H, 5.6, %Cl, 12.4.

STEP C: 3-(1'-methyl-2'-hydroxy-3'-chloropropyl)-benzhydrol

Using the procedure of Step B of Example XVI, 3-(1'-methyl-2'-oxo-3'-chloropropyl)-benzophenone was reacted to form 3-(1'-methyl-2'-hydroxy-3'-chloropropyl)-benzhydrol which was used as is for the next step. For analysis, a portion of the raw product was chromatographed over silica gel to obtain an oil soluble in methylene chloride, chloroform and alcohols.

Analysis: $C_{17}H_{19}ClO_2$; molecular weight = 290.78. Calculated: %C, 70.22; %H, 6.58; %Cl, 12.19. Found: %C, 70.1; 6.6; %Cl, 12.1.

STEP D:

Using the procedure of Step C of Example XVI, 3-(1'-methyl-2'-hydroxy-3-chloropropyl)-benzhydrol was reacted to form 3-(1'-methyl-2'-hydroxy-3'-cyanopropyl)-benzhydrol.

Analysis: $C_{18}H_{19}NO_2$; molecular weight = 281.35. Calculated: %C, 76.84; %H, 6.81; %N, 4.98. Found: %C, 76.7; %H, 6.8; %N, 4.6.

STEP E:

Using the procedure of step D of Example XVI, 3-(1'-methyl-2'-hydroxy-3'-cyanopropyl)-benzhydrol was reacted to form 3-(1'-methyl-2'-hydroxy-3'-cyanopropyl)-benzophenone melting at 130° C.

Analysis: $C_{18}H_{17}NO_2$; molecular weight = 279.34. Calculated: %C, 77.39; %H, 6.13; %N, 5.01. Found: %C, 77.5; %H, 6.3; %N, 5.2.

STEP F:

Using the process of Step E of Example XVI, 3-(1'-methyl-2'-hydroxy-3'-cyanopropyl)-benzophenone was reacted to form ethyl 4-(m-benzoyl-phenyl)-3-hydroxy-4-methyl-butyrate in the form of an oil soluble in chloroform, methylene chloride and alcohols.

Analysis: $C_{20}H_{22}O_4$; molecular weight = 326.39. Calculated: %C, 73.60; %H, 6.79. Found: %C, 73.8; %H, 7.0.

I.R. Spectrum (chloroform): Ester carbonyl at $1725^{cm-1}$, conjugated ketone at $1661^{cm-1}$, and aromatic at 1601, 1573 and $1473^{cm-1}$. Absence of C≡N.

EXAMPLE XX

A mixture of 818 mg of ethyl 4-(m-benzoyl-phenyl)-3-hydroxy-4-methyl-butyrate, 8 ml of ethanol, 0.8 ml of water and 0.2 ml of 14N potassium hydroxide was refluxed for 1½ hours and then was evaporated to dryness under reduced pressure. The residue was taken up in 20 ml of water and the solution was acidified to a pH of 1 by progressive addition of a 1N hydrochloric acid solution and was then extracted with methylene chloride. The organic phase was washed with water and evaporated to dryness under reduced pressure to obtain 4-(m-benzoyl-phenyl)-3-hydroxy-4-methyl-butyric acid in the form of a product soluble in alcohols, methylene chloride and chloroform.

Analysis: $C_{18}H_{18}O_4$; molecular weight = 298.34. Calculated: %C, 72.46 %H, 6.08. Found: %C, 72.3 %H, 6.0.

I.R. Spectrum (chloroform): Acid carbonyl at $1718^{cm-1}$, acid OH at $3494^{cm-1}$, OH at $3575^{cm-1}$ aromatic at 1601, 1582 and $1482^{cm-1}$ and CO at $1658^{cm-1}$.

EXAMPLE XXI

STEP A: 3-(2'-ethoxy carbonyl-3'-oxo-butyl)-benzophenone

Dry sodium ethylate prepared from 2.51 g of sodium was added to 125 ml of anhydrous benzene and 13.5 ml of ethyl acetylacetate at 20° C and after heating at 100° C for 15 minutes, 27.5 g of 3-bromomethyl-benzophenone were added all at once. The reaction mixture was refluxed for 3 hours and after cooling to 20° C, the benzene solution was washed twice with 25 ml of 2N hydrochloric acid and then with water until the wash water was neutral. The solution was dried over sodium sulfate and evaporated to dryness under reduced pressure to obtain 33.8 g of raw product which was chromatographed over silica gel and was eluted with a 50-50 mixture of ether-petroleum ether (B.P. of 40°–60° C) to obtain 15.3 g of 3-(2'-oxo-3'-ethoxycarbonyl-butyl)-benzophenone in the form of a marron resin which was used as is for the next step.

STEP B: 3-(3'-oxo-butyl)-benzophenone

A mixture of 14.2 g of 3-(2'-oxo-3'-ethoxycarbonyl-butyl)-benzophenone and 142 ml of 6N hydrochloric acid was refluxed with stirring of 17 hours and after cooling to 20° C, the mixture was diluted with 140 ml of water and extracted 3 times with 50 ml of methylene chloride. The organic phase was washed with 50 ml of an aqueous saturated sodium bicarbonate solution and twice with 50 ml of water, dried over sodium sulfate and evaporated to dryness under reduced pressure to obtain 10.76 g of 3-(3'-oxo-butyl)-benzophenone which was utilized as is for the next step.

STEP C: 4-(m-benzoyl-phenyl)-butyric acid

A mixture of 3.15 g of product of Step B, 400 mg of sulfur, 2.5 ml of morpholine and 50 mgof p-toluene sulfonic acis was refluxed for 3 hours and after cooling to room temperature, a mixture of 75 ml of acetic acid, 25 ml of sulfuric acid and 15 ml of water was added thereto. The mixture was refluxed for 15 hours, cooled to 20° C and added to water. The mixture was extracted with methylene chloride and the extracts were evaporated to dryness. The residue was purified by crystallization from isopropyl ether to obtain 4-(m-benzoyl-phenyl)-butyric acid, identical to the product of Example I.

EXAMPLE XXII

A solution of 6.2 g of ethyl 4-(m-benzoyl-phenyl)-4-methyl-3-hydroxy-butyrate (by process of Step E of Example XIX) in 60 ml of pyridine was heated at 100° C for 3 hours in the presence of 5 ml of phosphorus oxychloride and was then poured into a mixture of 200 g of ice and 65 ml of concentrated hydrochloric acid. The mixture was extracted with ether and the ether phase was washed with water, then with an aqueous saturated sodium bicarbonate solution and then water until the wash water was neutral. The solution was dried over sodium sulfate, treated with activated carbon, filtered and evaporated to dryness under reduced pressure to obtain 5.35 g of ethyl 4-(m-benzoyl-phenyl)-4-methyl-3-butenoate.

A mixture of 5.35 g of the said ester in 50 ml of methanol and 20 ml of 2N sodium hydroxide were refluxed for 2 hours and then the methanol was distilled off. The mixture was added to water, treated with activated carbon and filtered. The filtrate was acidified with 3 ml of concentrated hydrochloric acid and was extracted with ether. The ether extract was washed with water until the wash water was neutral, dried over sodium sulfate and evaporated to dryness under reduced pressure to obtain 4.31 g of 4-(m-benzoyl-phenyl)-4-methyl-3-butenoic acid.

EXAMPLE XXIII

Hydrogen was bubbled through a mixture of 2.2 g of 4-(m-benzoyl-phenyl)-4-methyl-3-butenoic acid and 22 ml of ethanol in the presence of 2.2 g of Raney nickel and after filtering, the mixture was evaporated to dryness under reduced pressure. The residue was taken up in ether and the solution was extracted with dilute sodium hydroxide. The aqueous phase was treated with hydrochloric acid and was extracted with ether. The ether phase was washed with water, dried over sodium sulfate, treated with activated carbon, filtered and evaporated to dryness under reduced pressure to obtain 1.96 g of 4-(m-benzoyl-phenyl)-4-methyl-butyric acid in the form of an amorphous product.

EXAMPLE XXIV

STEP A: 2-methyl-3-nitro-4'-fluorobenzophenone 150 g of aluminum chloride were added over 30 minutes at 40° C under an argon atmosphere to a suspension of 107.8 g of 2-methyl-3-nitro-benzoyl chloride (Step A — Example IV) in 450 ml of fluorobenzene and the mixture was held at this temperature for 41 hours. After icing, the mixture was added to 1 liter of ice water and 250 ml of concentrated hydrochloric acid and after stirring for 30 minutes, the mixture was extracted with methylene chloride. The extract was washed with water, then with N sodium hydroxide and then with water until the wash water was neutral. The solution was dried over magnesium sulfate, treated with activated carbon, filtered and evaporated to dryness under reduced pressure to obtain 115.7 g of 2-methyl-3-nitro-4'-fluorobenzophenone in the form of white crystals. For analysis, a sample of the product was crystallized from n-pentane and had a melting point of 64° C.

Analysis: $C_{14}H_{10}FNO_3$; molecular weight = 259.64. Calculated: %C, 64.86; %H, 3.89; %F, 7.33; %N, 5.40. Found: %C, 65.0; %H, 3.8; %F, 7.4; %N, 5.6.

STEP B: 2-methyl-3-amino-4'-fluorobenzophenone-hydrochloride 38 ml of hydrochloric acid, 23 g of activated carbon and 12 ml of a solution of 20% palladium chloride in water were added to a solution of 114.7 g of 2-methyl-3-nitro-4'-fluorobenzophenone in 1 liter of ethanol and then a current of hydrogen was passed therethrough for 3 hours. The reaction mixture was filtered and the filter was rinsed with ethanol. The filtrate was concentrated until crystallization began and was iced and then vacuum filtered. The precipitate was empasted with ethanol and dried under reduced pressure to obtain 59.5 g of 2-methyl-3-amino-4'-fluorobenzophenone in the form of white crystals melting at 170° C. Evaporation of the mother liquor and treatment with isopropyl ether gave another 50.5 g of product for a total of 110 g. For analysis, a sample of the product was crystallized from an aqueous solution of 5% hydrochloric acid and melted at 170° C.

Analysis: $C_{14}H_{13}ClFNO$; molecular weight = 265.72. Calculated: %C, 63.28; %H, 4.93; %Cl, 13.34; %F, 7.15; %N, 5.27. Found: %C, 63.6; %H, 5.1; %Cl, 13.3; %F, 7.0; %N, 5.3.

STEP C: 1-chloro-4-(3'-p-fluorobenzoyl-2'-methyl-phenyl)-butene-2

30 ml of hydrochloric acid were added at 5° C to a suspension of 26.57 g of 2-methyl-3-amino-4'-fluorobenzophenone hydrochloride in 250 ml of water and then 7.5 g of sodium nitrite were added thereto with stirring to obtain a solution of 2-methyl-4'-fluorobenzophenone-3-diazonium chloride.

A solution of 60 g of sodium acetate, 5 g of cuprous chloride in 25 ml of water and 150 ml of acetone was cooled to −10° C and then 140 ml of 1,3-butadiene followed by the above solution of the diazonium chloride were added thereto. The temperature was returned to room temperature and the pH of the mixture was adjusted to 4 by addition of sodium acetate. The mixture was extracted with ether and the ether phase was washed with water, then with N sodium hydroxide and with water until the wash water was neutral. The ether phase was dried over magnesium sulfate, treated with activated carbon, filtered and evaporated to dryness by distillation under reduced pressure. The residue was chromatographed over silica gel and was eluted with methylene chloride which was evaporated to obtain 13.70 g of 1-chloro-4-(3'-p-fluorobenzoyl-2'-methyl-phenyl)-butene-2. The product was crystallized from refluxing pentane for analysis and melted at 67° C.

Analysis: $C_{18}H_{16}ClFO$; molecular weight = 302.78. Calculated: %C, 71.40; %H, 5.33; %Cl, 11.71; %F, 6.28. Found: %C, 71.2; %H, 5.3; %Cl, 11.8; %F, 6.3.

STEP D: 1-acetoxy-4-(3'-p-fluorobenzoyl-2'-methyl-phenyl)-butene-2

A solution of 6 g of 1-chloro-4-(3'-p-fluorobenzoyl-2'-methyl-phenyl)-butene-2 and 6 g of potassium acetate in 60 ml of acetic acid was refluxed for 23 hours, and after cooling to room temperature, the mixture was added to water and extracted with ether. The ether extract was washed with water, with an aqueous saturated sodium bicarbonate solution and then with water until the wash water was neutral. The ether phase was dried over magnesium sulfate, treated with activated carbon, filtered and evaporated to dryness by distillation under reduced pressure. The residue was chromatographed over silica gel and was eluted with methylene chloride which was evaporated to obtain 5.96 g of 1-acetoxy-4-(3'-p-fluorobenzoyl-2'-methyl-phenyl)-butene-2 in the form of a yellow oil.

Analysis: $C_{20}H_{19}FO_3$; molecular weight = 326.37. Calculated: %C, 73.60; %H, 5.87; %F, 5.82. Found: %C, 73.6; %H, 5.9; %F, 5.9.

STEP E: 1-hydroxy-4-(3'-p-fluorobenzoyl-2'-methyl-phenyl) butene-2

A solution of 6.01 g of 1-acetoxy-4-(3'-p-fluorobenzoyl-2'-methyl-phenyl)-butene-2 in 30 ml of methanol and 30 ml of 2N sodium hydroxide was heated at 60° C for 1 hour and after eliminating the methanol by distillation, the mixture was extracted with ether. The ether phase was washed with water until the wash water was neutral, dried over magnesium sulfate, treated with activated carbon, filtered and evaporated to dryness under reduced pressure to obtain 5.15 g of 1-hydroxy-4-(3'-p-fluorobenzoyl-2'-methyl-phenyl)-butene-2 in the form of a yellow oil.

Analysis: $C_{18}H_{17}FO_2$; molecular weight = 284.33. Calculated: %C, 76.04; %H, 6.03; %F, 6.68. Found: %C, 76.2; %H, 6.3; %F, 6.5.

STEP F: 4-(3'-p-fluorobenzoyl-2'-methyl-phenyl)-butanol

A current of hydrogen was bubbled for 2 hours through a solution of 4.97 g of 1-hydroxy-4-(3'-p-fluorobenzoyl-2'-methyl-phenyl)-butene-2 in 50 ml of methanol containing 5 g of Raney nickel and the mixture was then filtered. The filtrate was evaporated to dryness under reduced pressure and the residue was taken up in methylene chloride. The organic solution was dried over magnesium sulfate, treated with activated carbon and evaporated to dryness by distillation under reduced pressure. The residue was chromatographed over silica gel and was eluted with an 8-2 methylene chloride acetone mixture to obtain 4.2 g of 4-(3'-p-fluorobenzoyl-2'-methyl-phenyl)-butanol in the form of a colorless oil.

Analysis: $C_{18}H_{19}FO_2$; molecular weight = 286.35. Calculated: %C, 75.50; %H, 6.69; %F, 6.63. Found: %C, 75.3; %H, 6.8; %F, 5.7.

STEP G: 4-(3'-p-fluorobenzoyl-2'-methyl-phenyl)-butyric acid 14 ml of a sulfochromic mixture titrating 26.5 g of chromic anhydride per 100 ml were added over 25 minutes at 10° C to a solution of 3.47 g of 4-(3'-p-fluorobenzoyl-2'-methyl-phenyl)-butanol in 35 ml of acetone and after returning the mixture to room temperature, the mixture was stirred overnight. The mixture was poured into ice water and vacuum filtered, was washed with water until the wash water was neutral and the precipitate recovered was dried over phosphoric acid and crystallized from cycloxane to obtain 3.02 g of 4-(3'-p-fluorobenzoyl-2'-methyl-phenyl)-butyric acid in the form of colorless crystals melting at 94° C.

Analysis: $C_{18}H_{17}FO_3$; molecular weight = 300.33. Calculated: %C, 71.99; %H, 5.70; %F, 6.33. Found: %C, 72.1; %H, 5.9; %F, 6.0.

EXAMPLE XXV

Using the process of Step C of Example XXIV, 2-methyl-3-amino-4'-chlorobenzophenone (Step B of Example IV) was reacted to successively obtain 2-methyl-4'-chlorobenzophenone-3-diazonium chloride and then 1-chloro-4-(3'-p-chlorobenzoyl-2'-methyl-phenyl)-butene-2.

The latter product was reacted by the process of Step D of Example XXIV to obtain 1-acetoxy-4-(3'-p-chlorobenzoyl-2'-methyl-phenyl)-butene-2 which was treated by the process of Step E of Example XXIV to obtain 1-hydroxy-4-(3'-p-chlorobenzoyl-2'-methyl-phenyl)-butene-2.

The latter product was oxidized with chromic anhydride to obtain 4-(3'-p-chlorobenzoyl-2'-methyl-phenyl)-butene-2-oic acid in the form of colorless crystals melting at 136° C.

Analysis: $C_{18}H_{15}ClO_3$; molecular weight = 314.77. Calculated: %C, 68.69; %H, 4.80; %Cl, 11.26. Found: %C, 68.7; %H, 4.9; %Cl, 11.5.

EXAMPLE XXVI

STEP A: 2-methoxy-3-methyl-4'-chlorobenzophenone

A solution of 195.9 g of 2-hydroxy-3-methyl-4'-chlorobenzophenone [Huston et al., JACS, Vol. 73, (1951), p. 2483] in 1 liter of dimethylformamide was added with stirring to a suspension of 40.8 g of sodium hydride in 200 ml of dimethylformamide and the mixture was stirred for 1 hour with cooling in an ice-water bath. Then, a solution of 170.4 g of methyl iodide in 800 ml of dimethylformamide was added thereto over 40 minutes and the mixture was then stirred for 16 hours in the ice-water bath. The mixture was filtered to remove insolubles and the filtrate was treated with activated carbon, filtered and was evaporated to dryness under reduced pressure. The residue was taken up in 1 liter of ether and 200 ml of water and the aqueous phase was reextracted with ether. The combined ether phases were washed with water, dried over magnesium sulfate, treated with activated carbon, filtered and evaporated to dryness. The residue was chromatographed over silica and was eluted with methylene chloride to obtain 171 g of 2-methoxy-3-methyl-4'-chlorobenzophenone in the form of colorless crystals melting at 43° C.

Analysis: $C_{15}H_{13}ClO_2$; molecular weight = 260.72. Calculated: %C, 69.10; %H, 5.03; %Cl, 13.60. Found: %C, 69.1; %H, 5.1; %Cl, 13.8.

STEP B: 2-methoxy-3-bromomethyl-4'-chlorobenzophenone

A mixture of 1.78 g of N-bromo-succinimide and 10 mg of benzoyl peroxide was added to a suspension of 2.6 g of 2-methoxy-3-methyl-4'-chlorobenzophenone in 15 ml of carbon tetrachloride and the solution was refluxed for 4 hours. The insolubles were removed by filtration and the filtrate was evaporated to dryness to obtain 3.32 g of 2-methoxy-3-bromomethyl-4'-chlorobenzophenone in the form of a clear yellow oil.

Analysis: $C_{15}H_{12}BrClO_2$; molecular weight = 339.62. Calculated: %C, 53.05; %H, 3.56; %Br, 23.53; %Cl, 10.44. Found: %C, 52.9; %H, 3.6; %Br, 23.7; %Cl, 10.2.

STEP C: ETHYL 2-methoxy-3-(p-chlorobenzoyl)-benzyl malonate

A solution of 108.4 g of ethyl malonate in 450 ml of dimethylformamide was added at 10° C to a suspension of 32.6 g of sodium hydride in 300 ml of dimethylformamide and the solution was held at 10° C until gas evolution ceased. Then, a solution of 202.1 g of 2-methoxy-3-bromomethyl-4'-chlorobenzophenone in 800 ml of dimethylformamide was slowly added thereto and after standing overnight at room temperature, the solution was treated with activated carbon, filtered and evaporated to dryness under reduced pressure. The residue was taken up in ether and then water. The aqueous phase was extracted with ether and the combined ether phases were washed with water, dried over magnesium sulfate, treated with activated carbon, filtered and evaporated to dryness under reduced pressure to obtain 237.6 g of ethyl 2-methoxy-3-(p-chlorobenzoyl)-benzyl-malonate in the form of an oil.

Analysis: $C_{22}H_{23}ClO_6$; molecular weight = 418.88. Calculated: %C, 63.08; %H, 5.53; %Cl, 8.46. Found: %C, 62.9; %H, 5.5; %Cl, 8.7.

STEP D: 2-methoxy-3-(p-chlorobenzoyl)-benzyl-malonic acid

A solution of 86.4 g of sodium hydroxide in 180 ml of water was added with stirring to a suspension of 226.6 g of ethyl 2-methoxy-3-(p-chlorobenzoyl)-benzyl-malonate in 2.8 liters of methanol and the mixture was refluxed for 3 hours and then was cooled to room temperature. The mixture was filtered and the precipitate recovered was washed with methanol, then with ether and dried. The residue was dissolved in 800 ml of water and the solution was washed with ether and acidified to a pH of 1 by addition of 0.5N hydrochloric acid. The acid precipitate formed was extracted with ether and the combined organic phases were washed with water, dried over magnesium sulfate, treated with activated carbon, filtered and evaporated to dryness under reduced pressure. The residue was crystallized from benzene to obtain 96.2 g of 2-methoxy-3-(p-chlorobenzoyl)-benzyl-malonic acid in the form of colorless crystals which melted at 142° C after crystallization from benzene.

Analysis: $C_{18}H_{15}ClO_6$; molecular weight = 362.77. Calculated: %C, 59.60; %H, 4.16; %Cl, 9.77. Found: %C, 59.7; %H, 4.2; %Cl, 9.8.

STEP E: 3-(3'-p-chlorobenzoyl-2'-methoxy-phenyl)-propionic acid 96.2 g of 2-methoxy-3-(p-chlorobenzoyl)-benzylmalonic acid were heated at 170°–195° C under an argon atmosphere and after the evolution of carbon dioxide gas, the mixture was cooled and added to 1 liter of ether. The acid mixture was extracted several times with 600 ml of a solution of 10% potassium carbonate and 150 ml of water. The combined aqueous phases were acidified with concentrated hydrochloric acid and the acid precipitate formed was extracted with ether. The combined ether phases were washed with water, dried over magnesium sulfate and evaporated to dryness under reduced pressure. The residue was crystallized from cyclohexane to obtain 56.8 g of 3-(3'-p-chlorobenzoyl-2'-methoxy-phenyl)-propionic acid in the form of colorless crystals.

Analysis: $C_{17}H_{15}ClO_4$; molecular weight = 318.77. Calculated: %C, 64.06; %H, 4.74; %Cl, 11.12. Found: %C, 64.0; %H, 4.7; %Cl, 11.1.

STEP F: 3-(3'-p-chlorobenzoyl-2'-methoxy-phenyl)-propionyl chloride

A solution of 5.1 g of 3-(3'-p-chlorobenzoyl-2'-methoxy-phenyl)-propionic acid in 25 ml of thionyl chloride was refluxed for 2½ hours and the excess thionyl chloride was distilled off. The residue was taken up in benzene and was evaporated to dryness to obtain 5.6 g of 3-(3'-p-chlorobenzoyl-2'-methoxy-phenyl)-propionyl chloride which was used as is for the next step.

STEP G: 2-methoxy-3-(4''-diazo-3''-oxo-butyl)-4'-chlorobenzophenone 112 ml of methylene chloride titrating 15.1 g/l liter of diazomethane were added to a solution of 5.6 g of the acid chloride from Step F in 40 ml of methylene chloride cooled to 0° C and the mixture was stirred overnight at room temperature then evaporated to dryness to obtain 6.1 g of 2-methoxy-3-(4''-diazo-3''-oxo-butyl)-4'-chlorobenzophenone which was used as is for the next step.

STEP H: 2,3-isopropylidenedioxypropyl 4-(3'-p-chlorobenzoyl-2'-methoxy-phenyl)-butyrate 2.5 ml of a solution of 1 g of silver benzoate in 12.5 ml of triethylamine were added dropwise with stirring to a solution of 6.1 g of the product of Step G in 35 ml of 2,2-dimethyl-4-hydroxy methyl-1,3-dioxolane at room temperature and after the evolution of nitrogen ceased, the reaction mixture was poured into water and extracted with ether. The combined organic phases were washed with water and evaporated to dryness by distillation of ether. The residue was chromatographed over silica gel and was eluted with a 7-3 mixture of benzene-ethyl acetate to obtain 4.25 g of 2,3-isopropylidenedioxypropyl 4-(3'-p-chlorobenzoyl-2'-methoxy-phenyl)-butyrate in the form of a colorless oil.

Analysis: $C_{24}H_{27}ClO_6$; molecular weight = 446.905. Calculated: %C, 64.49; %H, 6.09; %Cl, 7.93. Found: %C, 64.7; %H, 5.9; %Cl, 8.2.

EXAMPLE XXVII

A mixture of 4.46 g of 2,3-isopropylidenedioxypropyl 4-(3'-p-chlorobenzoyl-2'-methhoxy-phenyl)-butyrate (Example XXVI), 6.18 g of boric acid and 25 ml of methoxy ethanol was heated at 100° C for 2 hours and after cooling, the mixture was poured into water and extracted with ether. The combined ether phases were washed with water, dried over magnesium sulfate, treated with activated carbon, filtered and evaporated to dryness under reduced pressure. The residue was chromatographed over silica gel and was eluted with a 1-1 methylene chloride - acetone mixture to obtain 3.65 g of 2,3-dihydroxypropyl 4-(3'-p-chlorobenzoyl-2'-methoxy-phenyl)-butyrate in the form of a yellow oil.

Analysis: $C_{21}H_{23}ClO_6$; molecular weight = 406.87. Calculated: %C, 61.99; %H, 5.70; %Cl, 8.71. Found: %C, 61.8; %H, 6.0; %Cl, 8.5.

EXAMPLE XXVIII 2,3-ispropylidenedioxypropyl 4-(3'-p-chlorobenzoyl-2'-methoxy-phenyl)-butyrate (Example XXVI) was saponified to obtain 4-(3'-p-chlorobenzoyl-2'-methoxy-phenyl)-butyric acid.

PHARMACOLOGICAL STUDY

A. Anti-inflammatory Activity

The test used was that of Branceni, et al, slightly modified [Arch. Int. Pharmacodyn, Vol. 152 (1954), p. 15] and consisted of administering to rats weighing about 150 g a single injection of 1 mg of naphthoyheparamine (N.H.A.) into the plantain aponeurosus of the rear paw, the said injection provoking the formation of inflammatory edema. The products to be tested were orally administered in aqueous solution or suspension one hour before the irritant injection. The inflammation was measured by plethysmometry with an electric plethysmometer with the volume of the paw being measured immediately before and 2 hours after the irritant injection. The increase in paw volume between the two measurements represents the degree of inflammation and the average degree in each group of animals is expressed in absolute values and a percentage of the control animals.

Under these conditions, the standard active dose more accurately calculated for a product is the $DA_{40}$, the dose that diminishes the degree of inflammation by 40% of that of the controls. The products were administered at different doses and the results are reported in the following Tables.

| Products | Lots | Dose Administered in mg/kg | Increase of paw volume in 2 hours | % of Protection | $DA_{40}$ in mg/kg |
|---|---|---|---|---|---|
| 4-(m-benzoyl-phenyl)-butyric acid | Controls | 0 | 17.1 | — | |
| | Product | 50 | 4.6 | 73 | |
| | Controls | 0 | 18.6 | — | 5 |
| | Product | 5 | 11.4 | 39 | |
| | | 10 | 5.8 | 69 | |
| 2,3-isopropylidene-dioxypropyl 4-(3'-p-chlorobenzoyl-2'-methyl-phenyl-buty-rate | Controls | 0 | 28.6 | — | |
| | Product | 1 | 20.1 | 30 | |
| | Controls | 0 | 32.1 | — | 2.5 |
| | Product | 0.5 | 24.8 | 23 | |
| | | 2 | 25.3 | 22 | |
| | Controls | 0 | 21.3 | — | |
| | Product | 4 | 11.0 | 48 | |
| | | 8 | 7.1 | 67 | |
| 2,3-isopropylidene-dioxypropyl 4-(3'-p-chlorobenzoyl-phenyl)-butyrate | Controls | 0 | 31.3 | — | |
| | Product | 5 | 11.6 | 63 | |
| | Controls | 0 | 22.3 | — | 3 |
| | Product | 1 | 16.6 | 26 | |
| | | 2.5 | 14.8 | 34 | |
| 2,3-dihydroxypropyl 4-(3'-p-chlorobenzoyl-2'-methyl-phenyl)-butyrate | Controls | 0 | 32.1 | — | |
| | Product | 5 | 22.8 | 29 | |
| | Controls | 0 | 24.3 | — | |
| | Product | 10 | 11.4 | 53 | |
| | | 20 | 9.9 | 59 | 5 |
| | Controls | 0 | 26.6 | — | |
| | Product | 2.5 | 15.8 | 41 | |
| | Controls | 0 | 26.8 | — | |
| | Product | 2.5 | 20.6 | 23 | |
| | | 5 | 14.3 | 46 | |
| 2,3-dihydroxypropyl 4-(m-benzoyl-phenyl)-butyrate | Controls | 0 | 17.6 | — | |
| | Product | 5 | 10.9 | 38 | |
| | Controls | 0 | 24.5 | — | 8 |
| | Product | 2.5 | 19.5 | 20 | |
| | | 10 | 15.1 | 38 | |
| | Controls | 0 | 13.6 | — | |
| | Products | 25 | 5.4 | 61 | |
| 2,3-dihydroxypropyl 4-(3'-p-chlorobenzoyl)-phenyl)-butyrate | Controls | 0 | 24.0 | — | |
| | Product | 5 | 19.3 | 20 | |
| | Controls | 0 | 22.1 | — | 9 |
| | Product | 10 | 12.0 | 46 | |
| 4-(m-benzoyl-phenyl)-3-hydroxy-butyric acid | Controls | 0 | 27.0 | — | |
| | Product | 10 | 18.1 | 33 | |
| | Controls | 0 | 13.6 | — | 17 |
| | Product | 25 | 8.4 | 39 | |
| Ethyl 4-(m-benzoyl-phenyl)-3-hydroxy-butyrate | Controls | 0 | 20.8 | — | |
| | Product | 10 | 15.3 | 26 | |
| | Controls | 0 | 13.6 | — | 15 |
| | Product | 25 | 5.8 | 58 | |
| | | 50 | 4.4 | 65 | |
| 2,3-isopropylidene-dioxypropyl 4-(m-benzoyl-phenyl)-butyrate | Controls | 0 | 27.0 | — | |
| | Product | 10 | 23.4 | 13 | |
| | Controls | 0 | 13.6 | — | 15 |
| | Product | 25 | 5.1 | 62 | |
| | | 50 | 2.5 | 82 | |
| 4-(m-benzoyl-phenyl)-2-methyl-butyric acid | Controls | 0 | 17.3 | — | |
| | Product | 10 | 14.8 | 15 | |
| | Controls | 0 | 21.5 | — | 35 |
| | Product | 50 | 11.0 | 49 | |
| | | 100 | 9.5 | 56 | |
| 4-(3'-p-chlorobenzoyl-2'-methyl-phenyl)-butyric acid | Controls | 0 | 24.3 | — | |
| | Product | 10 | 22.0 | 9 | |
| | | 20 | 12.1 | 50 | |
| | Controls | 0 | 29.1 | — | 19 |
| | Product | 5 | 26.3 | 10 | |
| | | 10 | 21.8 | 25 | |
| 4-(3'-p-chlorobenzoyl-phenyl)-butyric acid | Controls | 0 | 22.4 | — | |
| | Product | 10 | 19.9 | 11 | |
| | Controls | 0 | 30.3 | — | 25 |
| | Product | 20 | 18.6 | 39 | |
| | Controls | 0 | 20.6 | — | |
| | Product | 50 | 11.5 | 44 | |
| 2,3-isopropylidene-dioxypropyl 4-(m-benzoyl-phenyl)-2-methyl- | Controls | 0 | 22.0 | — | |
| | Product | 10 | 16.6 | 25 | |

| Products | Lots | Dose Administered in mg/kg | Increase of paw volume in 2 hours | % of Protection | $DA_{40}$ in mg/kg |
|---|---|---|---|---|---|
| butyrate | | | | | |
| | Controls | 0 | 17.3 | — | 30 |
| | Product | 20 | 14.6 | 16 | |
| 2,3-isopropylidene-dioxypropyl 4-(m-benzoyl-phenyl)-2-methyl-butyrate | Controls | 0 | 21.6 | — | |
| | Product | 50 | 10.4 | 52 | |
| 2,3-dihydroxypropyl 4-(m-benzoyl-phenyl)-2-methyl-butyrate | Controls | 0 | 22.0 | — | |
| | Product | 10 | 16.0 | 27 | 40 |
| | Controls | 0 | 17.3 | — | |
| | Product | 20 | 11.8 | 32 | 40 |
| | Controls | 0 | 23.9 | — | |
| | Product | 40 | 13.9 | 42 | |
| | | 50 | 12.6 | 47 | |

B. Analgesic Effect

The test used was based on the fact noted by R. Koster et al (Fed. Proc., (1959) Vol. 18, p. 412) wherein the intraperitoneal injection of acetic acid causes in mice characteristic repeated stretching and twisting movements which can persist for more than 6 hours. Analgesics prevent or suppress this syndrome which, therefore, can be considered as externalization of a diffuse abdominal pain.

A solution of 0.6% acetic acid in water containing 10% arabic gum was used and the dose which release the syndrome under these conditions was 0.01 cc/gm, that is 60 mg/kg of acetic acid. The test compounds were administered orally one-half hour before the intraperitoneal injection of acetic acid, the mice having fasted since the night before the experiment. For each dose and for each control, which are obligatory for each test, a group of 5 animals was used. For each mouse, the stretchings were observed and counted and then added for the group of 5 during a period of 15 minutes starting immediately after the injection of acetic acid.

The following Table summarizes the results.

| Products Doses administered in mg/kg | % of Protection |||||||  $DA_{50}$ mg/kg |
|---|---|---|---|---|---|---|---|---|
| | 2 | 5 | 10 | 20 | 50 | 100 | 200 | |
| 4-(m-benzoyl-phenyl) butyric acid | | 45 | 60 | 51 | 77 | | | 10 |
| 2,3-isopropylidene-dioxypropyl 4-(3'-p-chlorobenzoyl-2'-methyl-phenyl)-butyrate | | 32 | 53 | 53 | 64 | | | 10 to 20 |
| 2,3-isopropylidene-dioxypropyl 4-(3'-p-chlorobenzoyl-phenyl)-butyrate | | 23 | 27 | 62 | 72 | | | 15 |
| 2,3-dihydroxypropyl 4-(3'-p-chlorobenzoyl-2'-methyl-phenyl)-butyrate | | 32 | 62 | 62 | 70 | | | 10 |
| 2,3-dihydroxypropyl 4-(m-benzoyl-phenyl)-butyrate | 28 | 21 | 51 | 42 | 61 | 78 | | 10 |
| 2,3-dihydroxypropyl 4-(3'-p-chloro-benzoyl-phenyl)-butyrate | | 24 | 42 | 41 | 63 | | | 30 |
| 4-(m-benzoyl-phenyl)-3-hydroxy-butyric acid | 5 | 60 | 58 | 80 | 95 | | | 5 |
| ethyl 4-(m-benzoyl-phenyl)-3-hydroxy-butyrate | 4 | 44 | 42 | 66 | 90 | | | 15 |
| 2,3-isopropylidene-dioxypropyl 4-(m-benzoyl-phenyl)-butyrate | | | | 37 | 44 | 76 | | 50 |
| 4-(m-benzoyl-phenyl)-2-methyl-butyric acid | | | 31 | 45 | 50 | 87 | | 100 |
| 4-(3'-p-chlorobenzoyl-2'-methyl-phenyl)-butyric acid | | 33 | 57 | 82 | | | | 20 |
| 4-(3'-p-chlorobenzoyl-phenyl)-butyric acid | | | 17 | 53 | 68 | 76 | | 50 |
| 2,3-isopropylidene-dioxypropyl 4-(m-benzoyl-phenyl)-2-methyl-butyrate | | | | 50 | 44 | 70 | | 20 to 50 |
| 2,3-dihydroxypropyl 4-(m-benzoyl-phenyl)-2-methyl-butyrate | | | | 28 | 26 | 45 | | 200 |

C. Ulcerigenic Activity

The ulcerigenic activity was determined by a test inspired by Boissier et al. [Ther., Vol. 22 (1967), p. 157]. Female rats weighing between 120 and 140 g were starved for the 24 hours before the start of the test and the test products were administered orally in an aqueous suspension of 0.4 ml per 100 g of animal weight and at varying dosages. The animals were sacrificed 7 hours after the treatment or 31 hours after the beginning of starvation and the stomachs were removed. The importance of ulcerous lesions was evaluated for each stomach taking into account the number and sizes. The results are summarized in the following Table.

| Products | Average Ulcerigenic dose in mg/kg |
|---|---|
| 4-(m-benzoyl-phenyl)butyric acid | >300 |
| 2,3-isopropylidenedioxypropyl 4-(3'-p-chlorobenzoyl-2'-methyl-phenyl)-butyrate | >300 |
| 2,3-isopropylidenedioxypropyl 4-(3'-p-chlorobenzoyl-phenyl)-butyrate | >300 |
| 2,3-dihydroxypropyl 4-(3'-p-chlorobenzoyl-2'-methyl-phenyl)-butyrate | 300 |
| 2,3-dihydroxypropyl 4-(m-benzoyl-phenyl)-butyrate | 300 |
| 2,3-dihydroxypropyl 4-(3'-p-chlorobenzoyl-phenyl)-butyrate | >100 |
| 4-(m-benzoyl-phenyl)-3-hydroxy-butyric acid | 300 |
| Ethyl 4-(m-benzoyl-phenyl)-3-hydroxy-butyrate | >300 |
| 2,3-isopropylidenedioxypropyl |  |

-continued

| Products | Average Ulcerigenic dose in mg/kg |
|---|---|
| 4-(m-benzoyl-phenyl)-butyrate | >300 |
| 4-(3'-p-chlorobenzoyl-2'-methyl-phenyl)-butyric acid | >300 |
| 4-(3'-p-chlorobenzoyl-phenyl)-butyric acid | > 50 |

Various modifications of the products and methods of the invention may be made without departing from the spirit or scope thereof and it is to be understood that the invention is to be limited only as defined in the appended claims.

We claim:

1. An analgesic and anti-inflammatory composition comprising an effective amount of a compound selected from the group consisting of butyric acid derivative of the formula

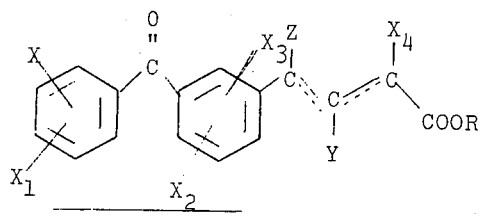

wherein X, $X_1$, $X_2$ and $X_3$ are individually selected from the group consisting of hydrogen, halogen, lower alkyl of 1 to 5 carbon atoms, lower alkoxy of 1 to 5 carbon atoms, lower alkylthio of 1 to 5 carbon atoms, trifluoromethoxy, trifluoromethylthio, trifluoromethyl, OH and dilower alkylamino of 1 to 5 carbon atoms for each alkyl, R is selected from the group consisting of hydrogen, lower alkyl of 1 to 5 carbon atoms, o-carboxyphenyl, 2,3-dihydroxypropyl and

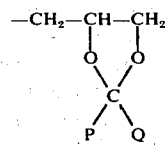

wherein P and Q are individually lower alkyl of 1 to 5 carbon atoms, Z and $X_4$ are individually selected from the group consisting of hydrogen and lower alkyl of 1 to 5 carbon atoms and Y is selected from the group consisting of hydrogen and —OH and the dotted line indicates the optional presence of a double bond when Y is hydrogen and when R is hydrogen or o-carboxyphenyl, a salt thereof with a non-toxic, pharmaceutically acceptable mineral or organic base and a pharmaceutical carrier.

2. A method of relieving pain and inflammation in warm-blooded animals comprising administering to a warm-blooded animal an effective amount of a compound selected from the group consisting of butyric acid derivative of the formula

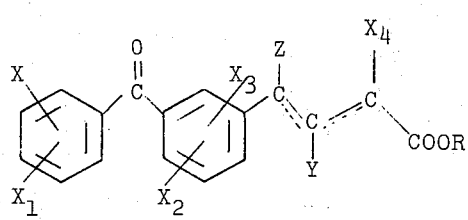

wherein X, $X_1$, $X_2$ and $X_3$ are individually selected from the group consisting of hydrogen, halogen, lower alkyl of 1 to 5 carbon atoms, lower alkoxy of 1 to 5 carbon atoms, lower alkylthio of 1 to 5 carbon atoms, trifluoromethoxy, trifluoromethylthio, trifluoromethyl, OH and dilower alkylamino of 1 to 5 carbon atoms for each alkyl, R is selected from the group consisting of hydrogen, lower alkyl of 1 to 5 carbon atoms, o-carboxyphenyl, 2,3-dihydroxypropyl and

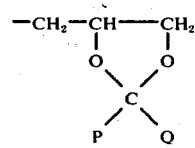

wherein P and Q are individually lower alkyl of 1 to 5 carbon atoms, Z and $X_4$ are individually selected from the group consisting of hydrogen and lower alkyl of 1 to 5 carbon atoms and Y is selected from the group consisting of hydrogen and —OH and the dotted line indicates the optional presence of a double bond when Y is hydrogen and when R is hydrogen or o-carboxyphenyl, a salt thereof with a non-toxic, pharmaceutically acceptable mineral or organic base.

3. The method of claim 2 wherein the compound is selected from the group consisting of 4-(3'-p-chlorobenzoyl-2'-methyl-phenyl)-butyric acid and 4-(3'-p-chlorobenzoyl-2'-methyl-phenyl)-2-butenoic acid.

4. The method of claim 2 wherein $X_1$ and $X_3$ are hydrogen, X and $X_2$ are individually selected from the group consisting of hydrogen, halogen, lower alkyl of 1 to 5 carbon atoms, lower alkoxy of 1 to 5 carbon atoms, lower alkylthio of 1 to 5 carbon atoms, trifluoromethoxy, trifluoromethylthio, trifluoromethyl, R is selected from the group consisting of hydrogen, alkyl of 1 to 5 carbon atoms, 2,3-dihydroxypropyl and

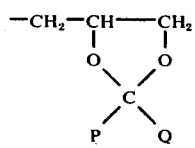

wherein P and Q are individually alkyl of 1 to 5 carbon atoms, and $X_4$, Z and Y have the definitions of claim 2.

5. The method of claim 4 wherein the compound has the formula

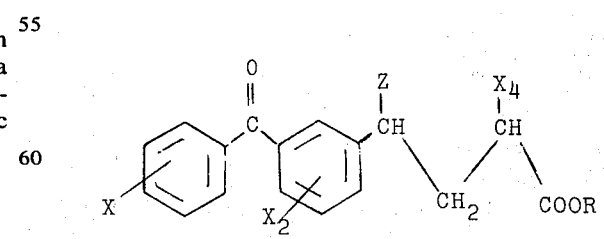

wherein X, $X_2$, $X_4$, Z and R have the definition of claim 4 and salts thereof where R is hydrogen.

6. The method of claim 4 wherein the compound has the formula

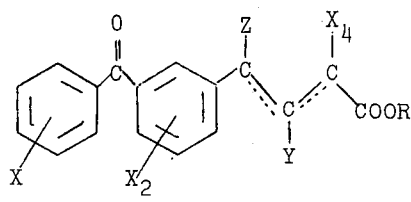

wherein X, $X_2$, $X_4$, Y, Z and R have the definition of claim 4 and the dotted line indicates the optional presence of a double bond, when Y is hydrogen, in either αβ or βγ to the carboxylic group and salts thereof where R is hydrogen.

7. The method of claim 4 wherein the compound has the formula

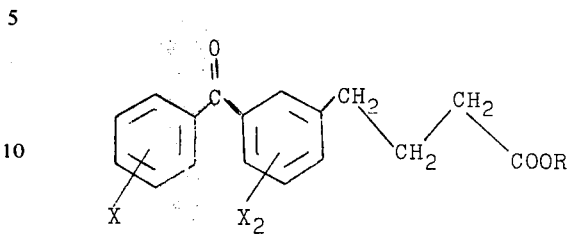

wherein X, $X_2$ and R have the definition of claim 4 and salts thereof where R is hydrogen.

* * * * *